US010111395B2

(12) United States Patent
Tadmor et al.

(10) Patent No.: US 10,111,395 B2
(45) Date of Patent: Oct. 30, 2018

(54) MELON PLANTS WITH ENHANCED FRUIT YIELDS

(71) Applicant: The State of Israel, Ministry of Agriculture & Rural Development, Agricultural Research Organization (ARO) (Volcani Center), Rishon-LeZion (IL)

(72) Inventors: Yaakov Tadmor, Timrat (IL); Yosef Burger, Haifa (IL); Ayala Meir, Givat Elah (IL); Uzi Saar, Kiryat-Tivon (IL); Fabian Baumkoler, Nazareth Ilit (IL); Arthur A. Schaffer, Hashmonaim (IL); Nurit Katzir, Kiryat-Tivon (IL); Ido Oz, Koranit (IL); Tamar Lavee, Zikhron-Yaakov (IL)

(73) Assignee: The State of Israel, Ministry of Agriculture & Rural Development, Agricultural Research Organizatin (ARO) (Volcani Center), Rishon-LeZion (IL)

( * ) Notice: Subject to any disclaimer, the term of this patent is extended or adjusted under 35 U.S.C. 154(b) by 0 days.

(21) Appl. No.: 15/125,172

(22) PCT Filed: Mar. 10, 2015

(86) PCT No.: PCT/IL2015/050252
§ 371 (c)(1),
(2) Date: Sep. 11, 2016

(87) PCT Pub. No.: WO2015/136532
PCT Pub. Date: Sep. 17, 2015

(65) Prior Publication Data
US 2017/0071145 A1    Mar. 16, 2017

Related U.S. Application Data

(60) Provisional application No. 61/950,315, filed on Mar. 10, 2014.

(51) Int. Cl.
*A01H 5/08*    (2018.01)
*C12Q 1/6895*    (2018.01)
*A01H 1/02*    (2006.01)
*A01H 4/00*    (2006.01)

(52) U.S. Cl.
CPC .............. *A01H 5/08* (2013.01); *A01H 1/02* (2013.01); *A01H 4/008* (2013.01); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2012/0324597 A1   12/2012   Tadmor et al.

FOREIGN PATENT DOCUMENTS

| CN | 1081335 | 2/1994 |
|----|---------|--------|
| CN | 1279009 | 1/2001 |
| CN | 103081704 | 5/2013 |
| CN | 103598076 | 2/2014 |
| KR | 10-2004-0082448 | 9/2004 |
| WO | WO 2011/018785 | 2/2011 |
| WO | WO 2015/136532 | 9/2015 |

OTHER PUBLICATIONS

International Preliminary Report on Patentability dated Oct. 17, 2016 From the International Bureau of WIPO Re. Application No. PCT/IL2015/050252. Corrected Version.
International Search Report and the Written Opinion dated Jun. 8, 2015 From the International Searching Authority Re. Application No. PCT/IL2015/050252.
Office Action dated Feb. 1, 2017 From the Israel Patent Office Re. Application No. 247707 and Its Translation Into English. (4 Pages).
Eukaryota et al. "Predicted: Zinc Finger Protein 8-like [Cucumis melo]", Database NCBI XP008443018; 1 Page, Jun. 25, 2014.
Grumet et al. "New Insights into Reproductive Development in Melon (Cucumis melo L.)" International Journal of Plant Developmental Biology, 1: 253-264, Dec. 31, 2007. p. 256-257.
Hayata et al. "CPPU and BA, With and Without Pollination, Affect Set, Growth, and Quality of Muskmelon Fruit", HortScience, 35(5):868-870, Aug. 31, 2000.
Levi et al. "Genes Expressed During the Development and Ripening of Watennelon Fruit", Plant Cell Rep, 25: 1233-1245, 2006.
Valantin et al. "Effect of Fruit Load on Partitioning of Dry Matter and Energy in Cantaloupe (Cucumis melo L.)", Annals of Botany, 84 (2): 173-181, Dec. 31, 1999. p. 173-175.
Supplementary European Search Report and the European Search Opinion dated Aug. 4, 2017 From the European Patent Office Re. Application No. 15761575.8. (10 Pages).
Galpaz et al. "Genetic and Chemical Characterization of an EMS Induced Mutation in Cucumis Melo CRTISO Gene", Archives of Biochemistry and Biophysics, XP028761605, 539(2): 117-125, Available Online Aug. 21, 2011 p. 118: Plant Material.
Notification of Office Action and Search Report dated Jan. 24, 2018 From the State Intellectual Property Office of the People's Republic of China Re. Application No. 201580024491.6 and Its Translation Into English. (21 Pages).
Jin et al. "Tey Techniques of Hybrid Seed Production of Seedless Thin Skin Melon 'Hatian No. 3'", Heilongjiang Agricultural Sciences, 7: 163-164, Dec. 31, 2011.

*Primary Examiner* — Brent T Page

(57) ABSTRACT

A *Cucumis melo* plant or a part thereof, the plant bearing more than 12 fruit, the fruit being seedless. Methods of generating same and breeding same are also disclosed.

23 Claims, 11 Drawing Sheets
(10 of 11 Drawing Sheet(s) Filed in Color)
Specification includes a Sequence Listing.

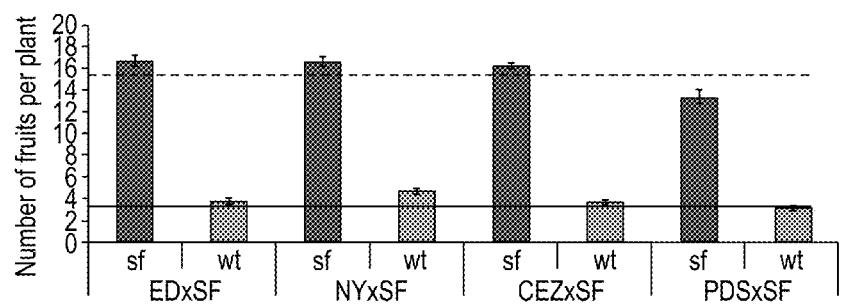
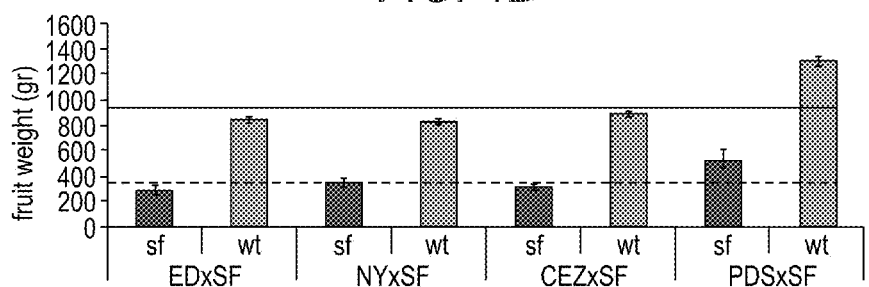
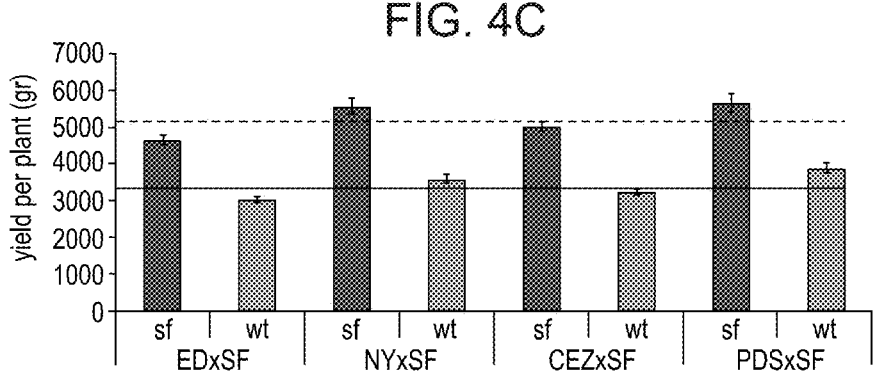

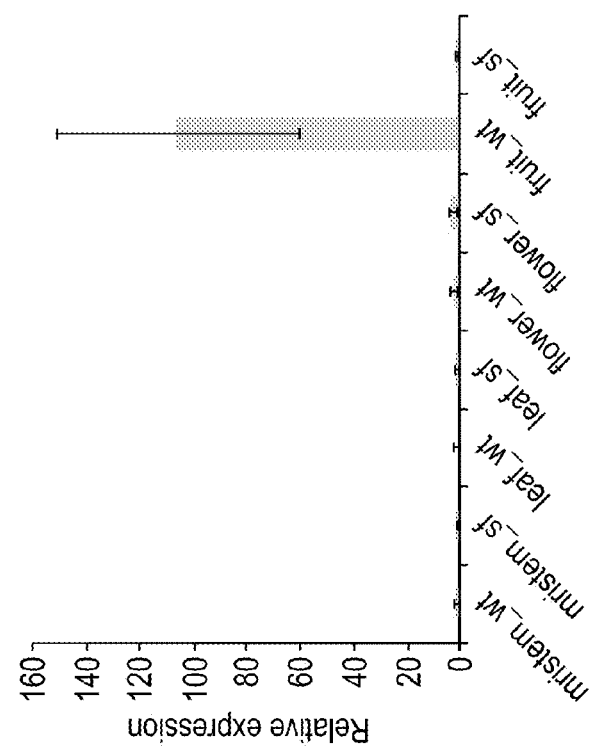
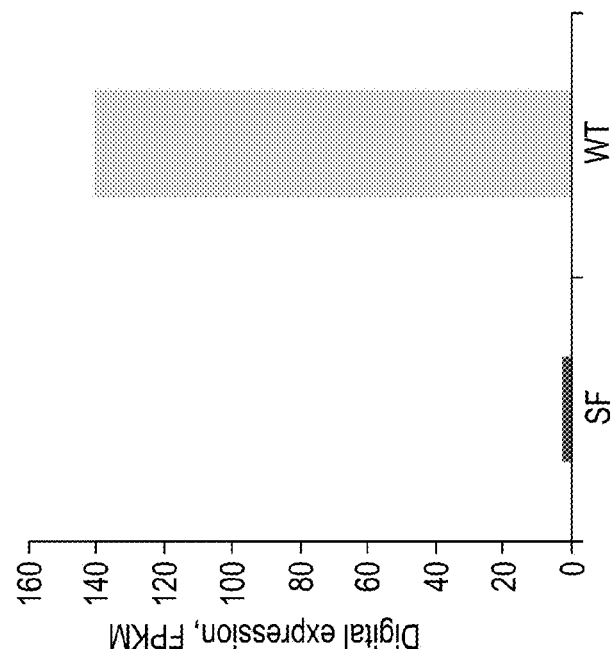

FIG. 11A

>MELO3C009603
TCTTCCTTTCTTCTTCTTCTTCTTCTCTGCCGTAACGATTGATATTAATTCTCTCCTCGGTGG
CGGCATAGGTTTTCAAAACCCCACGGCCCAACACCACCATATACACTTTCATGGACAAGAGTACCAGT
GAACGAGAGACTCATGATTTCATGAACGTCGAGTCTTTCTCTCAACTTCCCTTCATCCGTCCTGCACCAA
AAGAAAAGGGCATTAGGCTTTTCGGGATAGAATTTGGAAGTCGAAACGCTGCTACCGTCTCCGCTTCTTC
CATTGAGGAATCAGAGTCGGTGAAACTGTTATTGCATGCGAAGATGCGAAGAAAACAACGATGGC
AACAACAACAACGCGGAGAAGTAGCCGAGAGATTTGAAGTCATTACTGTTGTAGAAATTTCCCTACTT
CTCAAGCCTTAGGAGGACACCAAAATGCTCACAAAAGAGAGCGCAACATGCAAAAGGCTCACCTTCA
GTCTAACGCAGCCGCTATGGTTCATGGAATTGGACCCCTTTTCAGATGCGGCTCATGTCTATGGCCTCATG
AACTACCAACGCCTAGGCGCTACTCACCTTAATAATTACCCTTCTTGGAATAGAAATTCGCCAGCAGCAA
CGGCTGCTGCTGCTACAAGATTTTACGGTAGCTCTGGGCAGTATTCGTCGGCAGCAACCGC
GACGCCTATAAACGGGAGCCCGTTGGCGATGTGGAGAATCTCGGCGTTGTTTTCCGGAGATGAGATGAAAG
TCGTTTGGCGGTCGGAGCGGTCGTCCTCTACACCGTTGCCGGGTCCTCATCAGACTGGCCGGTT
GCGCTGGTGGTGGTGGCCACCGCCCGTTAGTGCCGGACCAACTGAGTTTGGATCTTCATCTGTAATAATTTAATTGACA
TGTTTACGAGGCAAAAACAGCGGACCAAGTGAGTTTGGATCTTCATCTGTAATAATTTAATTGACA
AATTTCTAAATTGACATGAATTTTCCTATAGACGATGAAAATTTTTTCATCTTCTTTTATATGCATTT
GCAAAGAGAGCAAAAAAAAAAAGAAAGAGACAAAATTCCGGCCGCTGGAGACGGATTTAATAAAACACTAA
TCGATCAAATATTTGTTTCTTC

FIG. 11B

MDKSTSERETHDFMNVESFSQLFFIRPAPKENGIRLFGIEFGSRNAATVSASSIEESESGETVIACEDAK
ENNDGNNNNGGESSRRFECR*CCR*IFTSALHCH/SNRKRERQHAKRAHLQSNAAAMVHGIGPFSDAA
HVYGLMNYQRIGATHLNNYPSWNPNSPAATAAAAATRFYGSSGGQYSSAATATPINGSPLAMWRISAVQ
NSNVPSSFGGRERSSLHPLPLFSGDEMMKGAGGGGGTAVSAGGSGGSHQTGRFVYEAKTADQVSLDLHL

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 1
aggctgattg tgctgtcctt                                          20

<210> SEQ ID NO 2
<211> LENGTH: 20
<212> TYPE: DNA
<213> ORGANISM: Artificial Sequence
```

```
<220> FEATURE:
<223> OTHER INFORMATION: Single strand DNA oligonucleotide

<400> SEQUENCE: 2
gatgggaacg aagggaattt                                                  20

<210> SEQ ID NO 3
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 3
tagacatgag ccgcatctga                                                  20

<210> SEQ ID NO 4
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 4
gaacgtggca acaacaacaa                                                  20

<210> SEQ ID NO 5
<211> LENGTH: 21
<212> TYPE: PRT
<213> ORGANISM: Artificial Sequence
<220> FEATURE:
<223> OTHER INFORMATION: Amino Acid sequence encoding the WT ZF motif of
      'sf' (MELO3C009603)

<400> SEQUENCE: 5

Cys His Tyr Cys Cys Arg Asn Phe Pro Thr Ser Gln Ala Leu Gly Gly
1               5                   10                  15

His Gln Asn Ala His
            20

<210> SEQ ID NO 6
<211> LENGTH: 21
<212> TYPE: PRT
<213> ORGANISM: Artificial Sequence
<220> FEATURE:
<223> OTHER INFORMATION: Amino Acid sequence encoding mutated ('F97' to
      'I' amino acid change)  ZF motif of 'sf' (MELO3C009603)

<400> SEQUENCE: 6

Cys His Tyr Cys Cys Arg Asn Ile Pro Thr Ser Gln Ala Leu Gly Gly
1               5                   10                  15

His Gln Asn Ala His
            20

<210> SEQ ID NO 7
<211> LENGTH: 1142
<212> TYPE: DNA
<213> ORGANISM: Cucumis melo

<400> SEQUENCE: 7
tcttcctttt ctttcttctt cttcttcttc ttctgccgta accgattgat attaattctc      60
tcctcggtgg cggcataggt ttttcaaaac cccacggccc caacaccacc atatacactt     120
tcatggacaa gagtaccagt gaacgagaga ctcatgattt catgaacgtc gagtctttct     180
```

```
ctcaacttcc cttcatccgt cctgcaccaa agaaaaggg cattaggctt ttcgggatag    240
aatttggaag tcgaaacgct gctaccgtct ccgcttcttc cattgaggaa tcagagtcgg    300
gtgaaactgt tattgcatgc gaagatgcga agaaaacaa caacgatggc aacaacaaca    360
acggcgagaa agtagccgg agatttgaat gtcattactg ttgtagaaat tccctactt    420 ctcaagcctt aggaggacac caaaatgctc acaaaagaga gcgccaacat gcaaaaggg    480 ctcaccttca gtctaacgca gccgctatgg ttcatggaat tggacccttt tcagatgcgg    540
ctcatgtcta tggcctcatg aactaccaac gcctaggcgc tactcacctt aataattacc    600
cttcttggaa tagaaattcg ccagcagcaa cggctgctgc tgctgctgct acaagatttt    660
acggtagctc tggtgggcag tattcgtcgg cagcaaccgc gacgcctata aacgggagcc    720
cgttggcgat gtgagaatc tcggccgttc aaaatagtaa tgtaccgtca tcgtttggcg    780
gtcgggagcg gtcgtctcta cacccgttgc cgttgttttc cggagatgag atgatgaaag    840
gcgctggtgg tggtggtggc accgccgtta gtgccggtgg gtccggcggg tctcatcaga    900
ctggccggtt tgtttacgag gcaaaaacag cggaccaagt gagtttggat cttcatctgt    960
aataatttaa ttaattgaca aatttctaaa ttgacatgaa ttttcctata gagatgatgg    1020
aaattttttc atcttctttt tatgtgcattt gcaaagaga gaaaaaaaaa agaaagagac    1080
aaaattccgg ccgctggaga cggatttaat aaaacactaa tcgatcaaat atttgtttct    1140
tc                                                                   1142
```

<210> SEQ ID NO 8
<211> LENGTH: 279
<212> TYPE: PRT
<213> ORGANISM: Artificial Sequence
<220> FEATURE:
<223> OTHER INFORMATION: An exemplary polypeptide sequence of a mutated
      MELO3C009603

<400> SEQUENCE: 8

```
Met Asp Lys Ser Thr Ser Glu Arg Glu Thr His Asp Phe Met Asn Val
1               5                   10                  15

Glu Ser Phe Ser Gln Leu Pro Phe Ile Arg Pro Ala Pro Lys Glu Lys
            20                  25                  30

Gly Ile Arg Leu Phe Gly Ile Glu Phe Gly Ser Arg Asn Ala Ala Thr
        35                  40                  45

Val Ser Ala Ser Ser Ile Glu Glu Ser Glu Ser Gly Glu Thr Val Ile
    50                  55                  60

Ala Cys Glu Asp Ala Lys Glu Asn Asn Asn Asp Gly Asn Asn Asn Asn
65                  70                  75                  80

Gly Gly Glu Ser Ser Arg Arg Phe Glu Cys His Tyr Cys Cys Arg Asn
                85                  90                  95

Ile Pro Thr Ser Gln Ala Leu Gly Gly His Gln Asn Ala His Lys Arg
            100                 105                 110

Glu Arg Gln His Ala Lys Arg Ala His Leu Gln Ser Asn Ala Ala Ala
        115                 120                 125

Met Val His Gly Ile Gly Pro Phe Ser Asp Ala Ala His Val Tyr Gly
    130                 135                 140

Leu Met Asn Tyr Gln Arg Leu Gly Ala Thr His Leu Asn Asn Tyr Pro
145                 150                 155                 160

Ser Trp Asn Arg Asn Ser Pro Ala Ala Thr Ala Ala Ala Ala Ala Ala
                165                 170                 175

Thr Arg Phe Tyr Gly Ser Ser Gly Gly Gln Tyr Ser Ser Ala Ala Thr
```

```
            180                 185                 190
Ala Thr Pro Ile Asn Gly Ser Pro Leu Ala Met Trp Arg Ile Ser Ala
            195                 200                 205

Val Gln Asn Ser Asn Val Pro Ser Ser Phe Gly Gly Arg Glu Arg Ser
    210                 215                 220

Ser Leu His Pro Leu Pro Leu Phe Ser Gly Asp Glu Met Met Lys Gly
225                 230                 235                 240

Ala Gly Gly Gly Gly Thr Ala Val Ser Ala Gly Ser Gly Gly
            245                 250                 255

Ser His Gln Thr Gly Arg Phe Val Tyr Glu Ala Lys Thr Ala Asp Gln
            260                 265                 270

Val Ser Leu Asp Leu His Leu
    275
```

<210> SEQ ID NO 9
<211> LENGTH: 1142
<212> TYPE: DNA
<213> ORGANISM: Artificial Sequence
<220> FEATURE:
<223> OTHER INFORMATION: exemplary polynucleotide sequence of a mutated
    MELO3C009603

<400> SEQUENCE: 9

```
tcttcctttt ctttcttctt cttcttcttc ttctgccgta accgattgat attaattctc       60
tcctcggtgg cggcataggt ttttcaaaac cccacggccc caacaccacc atatacactt      120
tcatggacaa gagtaccagt gaacgagaga ctcatgattt catgaacgtc gagtctttct      180
ctcaacttcc cttcatccgt cctgcaccaa agaaaaggg cattaggctt ttcgggatag       240
aatttggaag tcgaaacgct gctaccgtct ccgcttcttc cattgaggaa tcagagtcgg      300
gtgaaactgt tattgcatgc gaagatgcga agaaaacaa caacgatggc aacaacaaca      360
acggcggaga aagtagccgg agatttgaat gtcattactg ttgtagaaat atccctactt      420
ctcaagcctt aggaggacac caaaatgctc acaaaagaga gcgccaacat gcaaaagggg      480
ctcaccttca gtctaacgca gccgctatgg ttcatggaat tggacccttt tcagatgcgg      540
ctcatgtcta tggcctcatg aactaccaac gcctaggcgc tactcacctt aataattacc      600
cttcttggaa tagaaattcg ccagcagcaa cggctgctgc tgctgctgct acaagatttt      660
acggtagctc tggtgggcag tattcgtcgg cagcaaccgc gacgcctata aacgggagcc      720
cgttggcgat gtggagaatc tcggccgttc aaaatagtaa tgtaccgtca tcgtttggcg      780
gtcgggagcg tcgtctcta cacccgttgc cgttgttttc cggagatgag atgatgaaag      840
gcgctggtgg tggtggtggc accgccgtta gtgccggtgg gtccggcggg tctcatcaga      900
ctggccggtt tgtttacgag gcaaaaacag cggaccaagt gagtttggat cttcatctgt      960
aataatttaa ttaattgaca aatttctaaa ttgacatgaa ttttcctata gagatgatgg     1020
aaattttttc atcttctttt atatgcattt gcaaagaga gaaaaaaaaa agaaagagac     1080
aaaattccgg ccgctggaga cggatttaat aaaacactaa tcgatcaaat atttgtttct     1140
tc                                                                     1142
```

<210> SEQ ID NO 10
<211> LENGTH: 279
<212> TYPE: PRT
<213> ORGANISM: Cucumis melo

<400> SEQUENCE: 10

-continued

```
Met Asp Lys Ser Thr Ser Glu Arg Glu Thr His Asp Phe Met Asn Val
1               5                   10                  15

Glu Ser Phe Ser Gln Leu Pro Phe Ile Arg Pro Ala Pro Lys Glu Lys
                20                  25                  30

Gly Ile Arg Leu Phe Gly Ile Glu Phe Gly Ser Arg Asn Ala Ala Thr
                35                  40                  45

Val Ser Ala Ser Ser Ile Glu Glu Ser Glu Ser Gly Glu Thr Val Ile
    50                  55                  60

Ala Cys Glu Asp Ala Lys Glu Asn Asn Asn Asp Gly Asn Asn Asn Asn
65                  70                  75                  80

Gly Gly Glu Ser Ser Arg Arg Phe Glu Cys His Tyr Cys Cys Arg Asn
                85                  90                  95

Phe Pro Thr Ser Gln Ala Leu Gly Gly His Gln Asn Ala His Lys Arg
                100                 105                 110

Glu Arg Gln His Ala Lys Arg Ala His Leu Gln Ser Asn Ala Ala Ala
                115                 120                 125

Met Val His Gly Ile Gly Pro Phe Ser Asp Ala Ala His Val Tyr Gly
                130                 135                 140

Leu Met Asn Tyr Gln Arg Leu Gly Ala Thr His Leu Asn Asn Tyr Pro
145                 150                 155                 160

Ser Trp Asn Arg Asn Ser Pro Ala Ala Thr Ala Ala Ala Ala Ala Ala
                165                 170                 175

Thr Arg Phe Tyr Gly Ser Ser Gly Gly Gln Tyr Ser Ser Ala Ala Thr
                180                 185                 190

Ala Thr Pro Ile Asn Gly Ser Pro Leu Ala Met Trp Arg Ile Ser Ala
                195                 200                 205

Val Gln Asn Ser Asn Val Pro Ser Ser Phe Gly Gly Arg Glu Arg Ser
210                 215                 220

Ser Leu His Pro Leu Pro Leu Phe Ser Gly Asp Glu Met Met Lys Gly
225                 230                 235                 240

Ala Gly Gly Gly Gly Thr Ala Val Ser Ala Gly Gly Ser Gly Gly
                245                 250                 255

Ser His Gln Thr Gly Arg Phe Val Tyr Glu Ala Lys Thr Ala Asp Gln
                260                 265                 270

Val Ser Leu Asp Leu His Leu
                275
```

MELON PLANTS WITH ENHANCED FRUIT YIELDS

RELATED APPLICATIONS

This application is a National Phase of PCT Patent Application No. PCT/IL2015/050252 having International filing date of Mar. 10, 2015, which claims the benefit of priority under 35 USC § 119(e) of U.S. Provisional Patent Application No. 61/950,315 filed on Mar. 10, 2014. The contents of the above applications are all incorporated by reference as if fully set forth herein in their entirety.

SEQUENCE LISTING STATEMENT

The ASCII file, entitled 67549SequenceListing.txt, created on Sep. 11, 2016, comprising 10,428 bytes, submitted concurrently with the filing of this application is incorporated herein by reference.

FIELD AND BACKGROUND OF THE INVENTION

The present invention, in some embodiments thereof, relates to melon plants, having small seedless fruit with enhanced fruit yields and methods of generating same.

Parthenocarpy, the production of seedless fruits, can be achieved by the addition of the plant growth regulators auxin, cytokinin or gibberellin in many crops. It has been shown that the exogenous application of auxin or gibberellin to unfertilized flowers in a number of plant species, induces fruit set in the absence of pollination, resulting in the production of parthenocarpic fruit. In previous efforts to produce seedless fruits, traditional plant breeding and exogenous application of hormones have been used with some success. However, the exogenous application of plant hormones is a labor-intensive process, and traditional plant breeding is a long term process. Moreover, at least some of the previous attempts to produce certain seedless fruits have resulted in low numbers of seedless fruits and/or in relatively small seedless fruits as compared with the normal, seeded fruits. In most cases, this led to a significant yield reduction in small fruit varieties.

*Cucumis melo* exhibits extreme diversity for fruit traits. Melon fruit vary in size, shape, external color, aroma and flesh characters such as sugar content, acidity and pigmentation. Still, there is an increasing demand for new fruit types by modern food markets. In melon, fruit set and number is a trait that is mostly governed at the hormonal level. Fruit set is affected by hormonal talk that results from the success or failure of the previous female flower on the branch to develop a fruit however the general number of fruit per plant is pretty constant. Typically, most melon varieties will produce 1-5 fruit per plant in the field.

There is a long felt need in the art for an effective and economical means and methods for the production of seedless fruit, particularly in good yield and quality as compared with prior art seedless fruits.

Background art includes U.S. Patent Application No. 20120324597 and WO 2011/018785.

SUMMARY OF THE INVENTION

According to an aspect of some embodiments of the present invention there is provided a *Cucumis melo* plant or a part thereof, the plant bearing more than 12 fruit, said fruit being seedless.

According to an aspect of some embodiments of the present invention there is provided a *Cucumis melo* plant having a MELO3C009603/melo3c009603 genome such that upon self-pollination, 25% of F1 bear more than 12 fruit, said fruit being seedless.

According to an aspect of some embodiments of the present invention there is provided a cutting of a *C. melo* plant of the plants described herein.

According to an aspect of some embodiments of the present invention there is provided a seed of a *Cucumis melo* plant having a MELO3C009603/melo3c009603 genome such that upon self-pollination, 25% of F1 bear more than 12 fruit, said fruit being seedless.

According to an aspect of some embodiments of the present invention there is provided a cell having the genome of the any of the plants described herein.

According to an aspect of some embodiments of the present invention there is provided a culture comprising a plurality of the cells described herein.

According to an aspect of some embodiments of the present invention there is provided a method of breeding a first *C. melo* comprising crossing the plants described herein with a second *C. melo* plant, thereby breeding the *C. melo*.

According to an aspect of some embodiments of the present invention there is provided a plurality of *C. melo* seeds which are heterozygotic for a MELO3C009603 mutation which upon planting brings about an enhanced fruit crop phenotype in 25% of the plants derived therefrom.

According to an aspect of some embodiments of the present invention there is provided a hybrid seed produced by the methods described herein.

According to an aspect of some embodiments of the present invention there is provided a hybrid plant, or parts thereof, produced by growing the hybrid seed described herein.

According to an aspect of some embodiments of the present invention there is provided a method of growing any of the plants described herein comprising vegetatively propagating the plant, thereby growing the plant.

According to an aspect of some embodiments of the present invention there is provided an isolated polynucleotide comprising the sequence as set forth in SEQ ID NO: 9.

According to an aspect of some embodiments of the present invention there is provided an isolated polypeptide comprising a sequence as set forth in SEQ ID NO: 8.

According to an aspect of some embodiments of the present invention there is provided a method of marker assisted selection of a *C. melo* plant having improved fruit yield or having a progeny with improved yield, the method comprising analyzing for the presence of a loss of function mutation in at least one MELO3C009603 allele, wherein the presence of said mutation is indicative that the plant or progeny thereof will bear more than 5 seedless fruit.

According to an aspect of some embodiments of the present invention there is provided a food or processed product comprising the plants described herein or parts thereof.

According to some embodiments of the invention, the plant bears more than 15 fruit.

According to some embodiments of the invention, the plant bears more than 20 fruit.

According to some embodiments of the invention, the plant has a similar total soluble solid (TSS) content and β-carotene content as a wild-type *Cucumis melo* plant.

According to some embodiments of the invention, the weight of total fruit of the plant is greater than the weight of total fruit of a wild-type Cucumis melo plant.

According to some embodiments of the invention, the plant is of a variety C. melo Cantalupensis.

According to some embodiments of the invention, both alleles of MELO3C009603 of the genome of the plant have a loss of function mutation that results in a seedless trait.

According to some embodiments of the invention, both alleles of said MELO3C009603 have an F/I mutation at position 97 thereof.

According to some embodiments of the invention, the polynucleotide sequence of said MELO3C009603 is as set forth in SEQ ID NO: 7.

According to some embodiments of the invention, the polypeptide sequence of MELO3C009603 is as set forth in SEQ ID NO: 8.

According to some embodiments of the invention, the plant part is selected from the group consisting of roots, stems, leaves, cotyledons, flowers, fruit, embryos and pollen.

According to some embodiments of the invention, the crossing comprising pollinating.

According to some embodiments of the invention, the subspecies of said melo plant is selected from the group consisting of melo Cantalupensis, Noy Yizre'el, Ein Dor and Piel De Sapo.

According to some embodiments of the invention, the second C. melo plant is not any of the plants described herein (e.g. doesn't have a mutation in MELO3C009603).

According to some embodiments of the invention, 25% of the plants bear more than 5 fruit, the fruit being seedless.

According to some embodiments of the invention, the marker assisted selection is conducted using an assay selected from the group consisting of single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, and Flap Endonuclease-mediated assays.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIGS. 4A-C are bar graphs illustrating the field performance of 'sf' and wild type $F_2$ segregants derived from four independent crosses. Horizontal continuous and broken lines represents mean values of all wild types and 'sf' respectively. A—average fruit number; B—average fruit weight; C— average fruit weight per plant (yield).

Figure 5A:
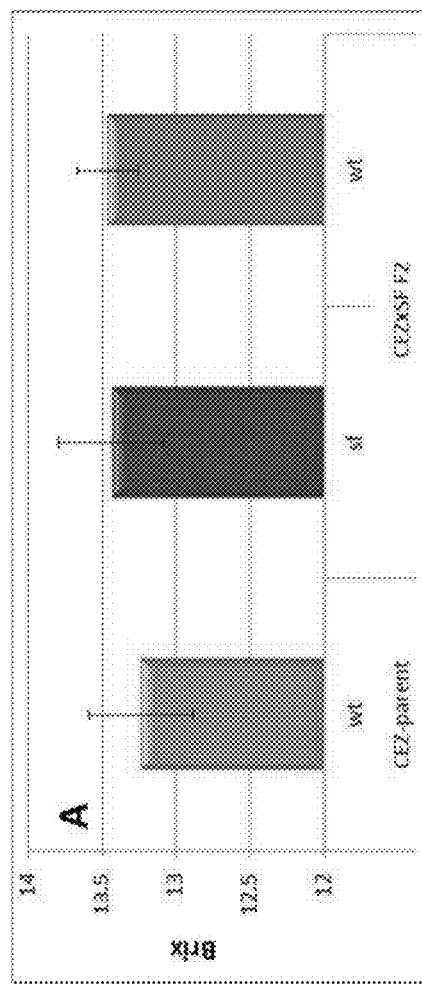
Figure 5B:
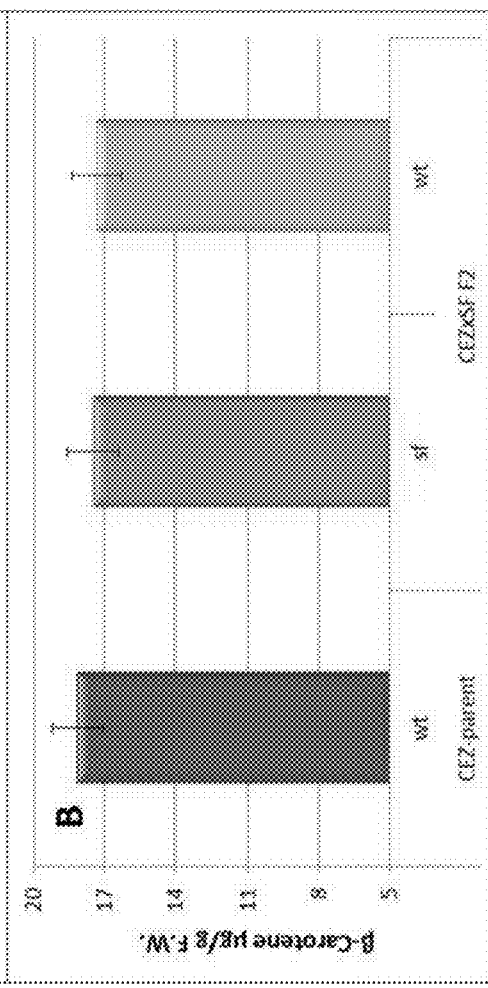

FIGS. 5A-B are bar graphs illustrating the quality of 'sf' and wild type $F_2$ segregants from CEZ x 'sf' cross. A—Average Brix (TSS) of 10 fruit of CEZ, 'sf' and wildtype segregants; B—Average β-carotene content of 10 fruit of CEZ, 'sf' and wildtype segregants.

Figure 6:
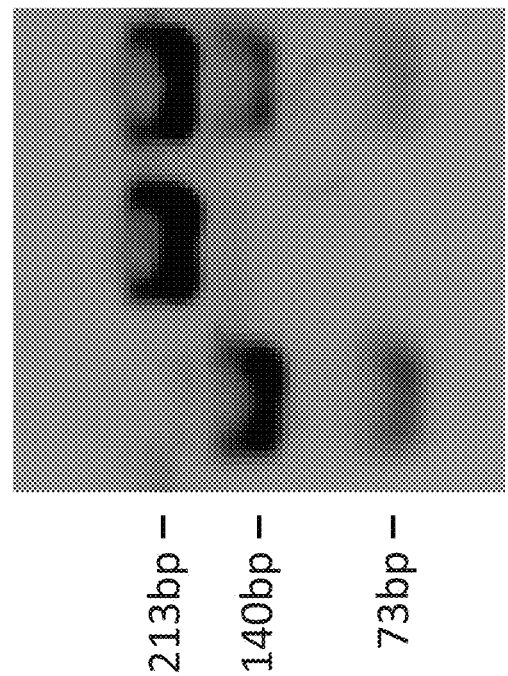

FIG. 6 is a photograph of ApoI digestion products of a 213 base pairs (bp) PCR product amplified from DNA of (from left to right) 'sf', 'CEZ' and their $F_1$ plants. The size in base pairs (bp) of the DNA fragments appears on the left. Forward primer TAGACATGAGCCGCATCTGA (SEQ ID NO: 3) and reverse primer GAACGTG-GCAACAACAACAA (SEQ ID NO: 4) were utilized for the PCR amplification.

Figure 7:
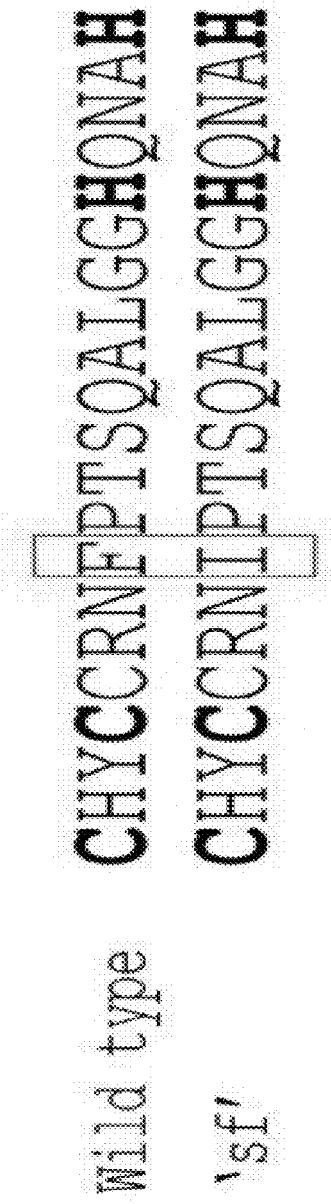

FIG. 7 is an alignment of the 'Zing Finger' (ZF) motif of 'sf' (MELO3C009603) showing the '$F^{97}$' to 'I' amino acid change (red frame). The two Cysteine and Histidine amino acids of the $C_2H_2$ are bolded. CHYCCRNFPTSQALG-GHQNAH (SEQ ID NO: 5); CHYCCRNIPTSQALGGHQ-NAH (SEQ ID NO: 6).

Figure 8:
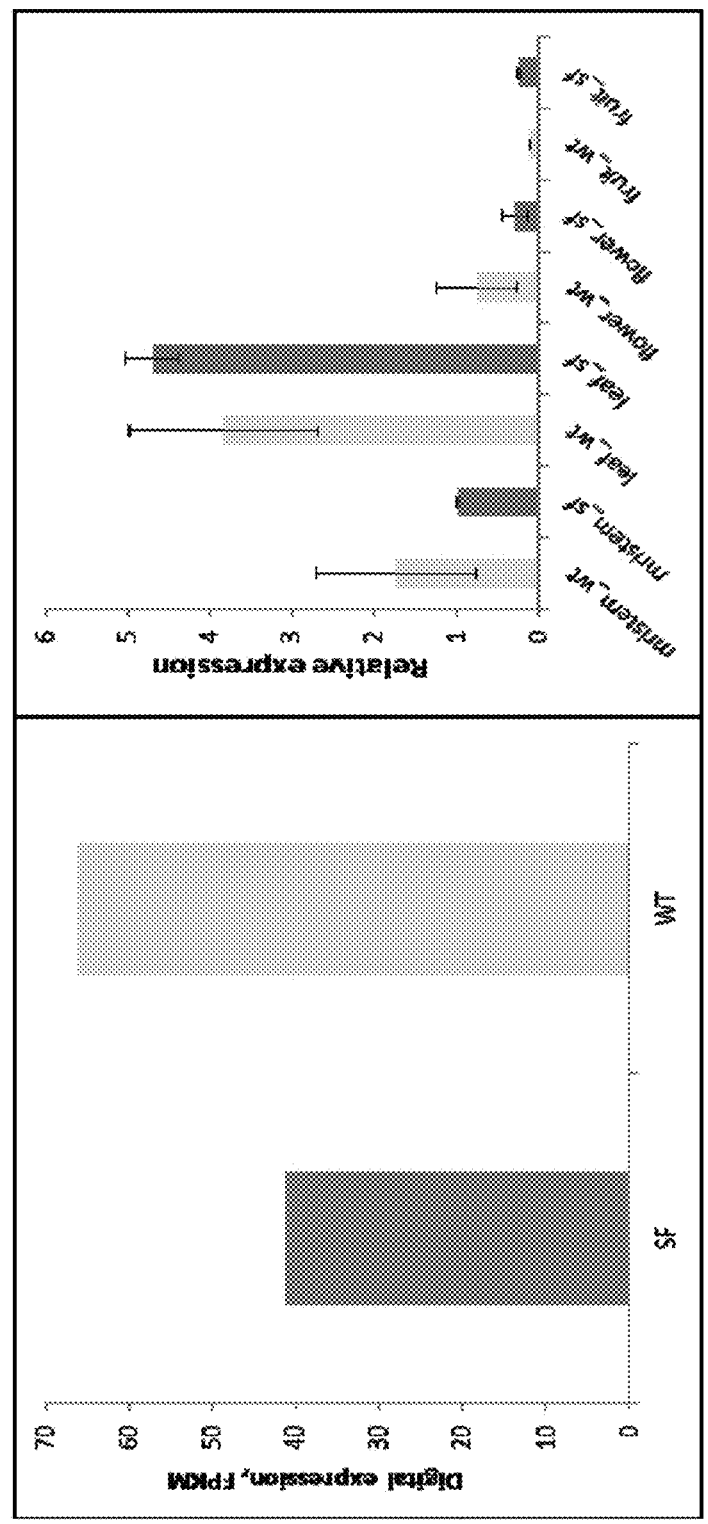

FIGS. 8A-B are graphs illustrating the expression of MELO3C009603 (sf gene). FIG. 8A—RNA-Seq based digital expression of MELO3C009603 (sf gene) in 'sf' and wild type bulks; FIG. 8B—qualitative-RTPCR analysis of relative expression (APR1 gene as a reference) of MELO3C009603 in the tissues that comprised each of the bulks.

Figure 9:
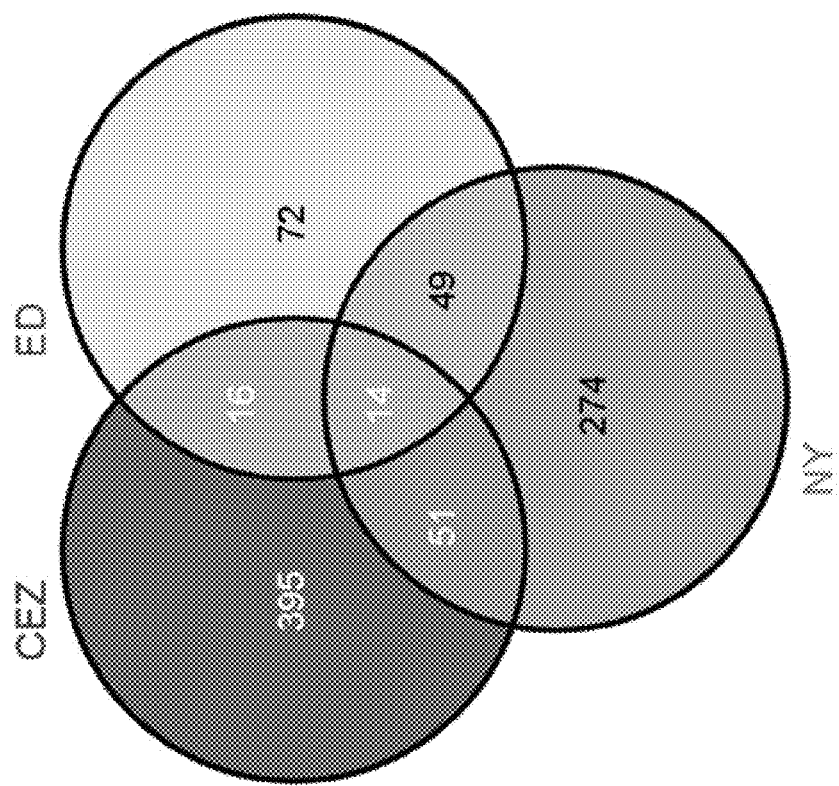

FIG. 9 is a Venn diagram showing all differentially expressed genes (DEG) in the three segregating populations and the overlapping ones.

FIG. 10A is a graph illustrating RNA-Seq based digital expression of MELO3C021150 (seed nucellus gene) in isogenic 'sf' and wild type (CEZ) bulks;

FIG. 10B is a graph illustrating relative expression of MELO3C021150 in the tissues that comprised the isogenic bulks, analyzed by qRTPCR (APR1 gene as a reference).

FIGS. 11A-B provides the wild type complementary DNA sequence (FIG. 11A—SEQ ID NO: 7) and the mutated amino acid sequence (FIG. 11B—SEQ ID NO: 8) of MELO3C009603 in the mutated plants. FIG. 11A. The first ATG is highlighted in yellow and the TAA stop codon is highlighted in red. 'TTC' that codes for 'F' in wild type is bolded and the 'T' that is mutated to an 'A' in 'sf' is colored red; FIG. 11B—Protein sequence of 'sf' gene. The zinc finger domain colored blue, $C_2$ and $H_2$ green and the mutated amino acid 'I' in red. QAALGH motif within the ZF domain is underlined.

DESCRIPTION OF SPECIFIC EMBODIMENTS OF THE INVENTION

The present invention, in some embodiments thereof, relates to melon plants, having enhanced fruit yields and methods of generating same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Among Cucurbitaceae, *C. melo* is one of the most important cultivated cucurbits. They are grown primarily for their fruit, which generally have a great diversity in size (500 g to 5 kg), flesh color (orange, green, and white), rind color (green, yellow, white, orange, and gray), shape (round, oval, and elongated), and dimension (5 to 25 cm wide; 10 to 50 cm long).

Figure 1:
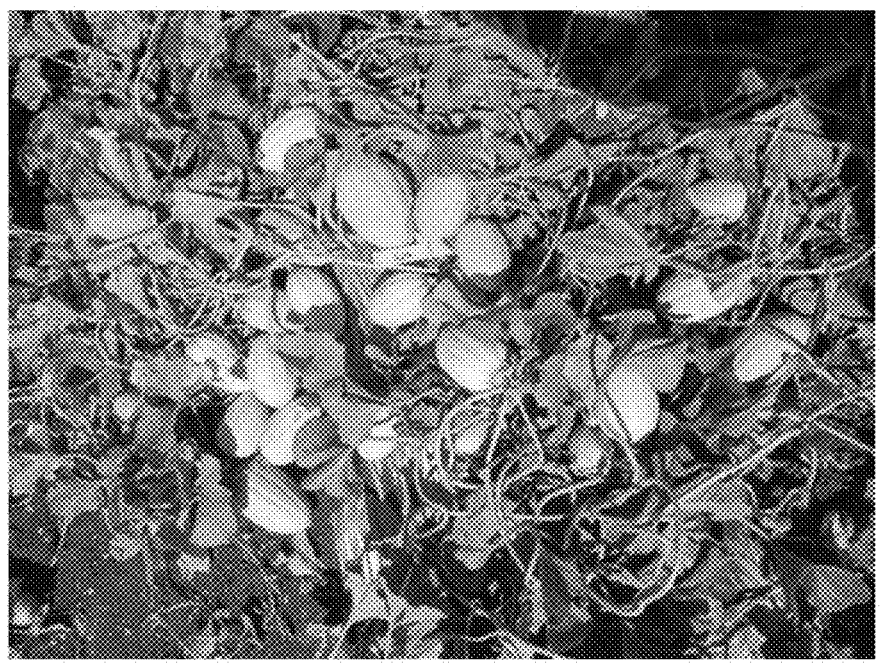
FIG. 1 is a photograph of a 'superfruiter' ('sf') plant bearing fruit in the field.
Figure 2:
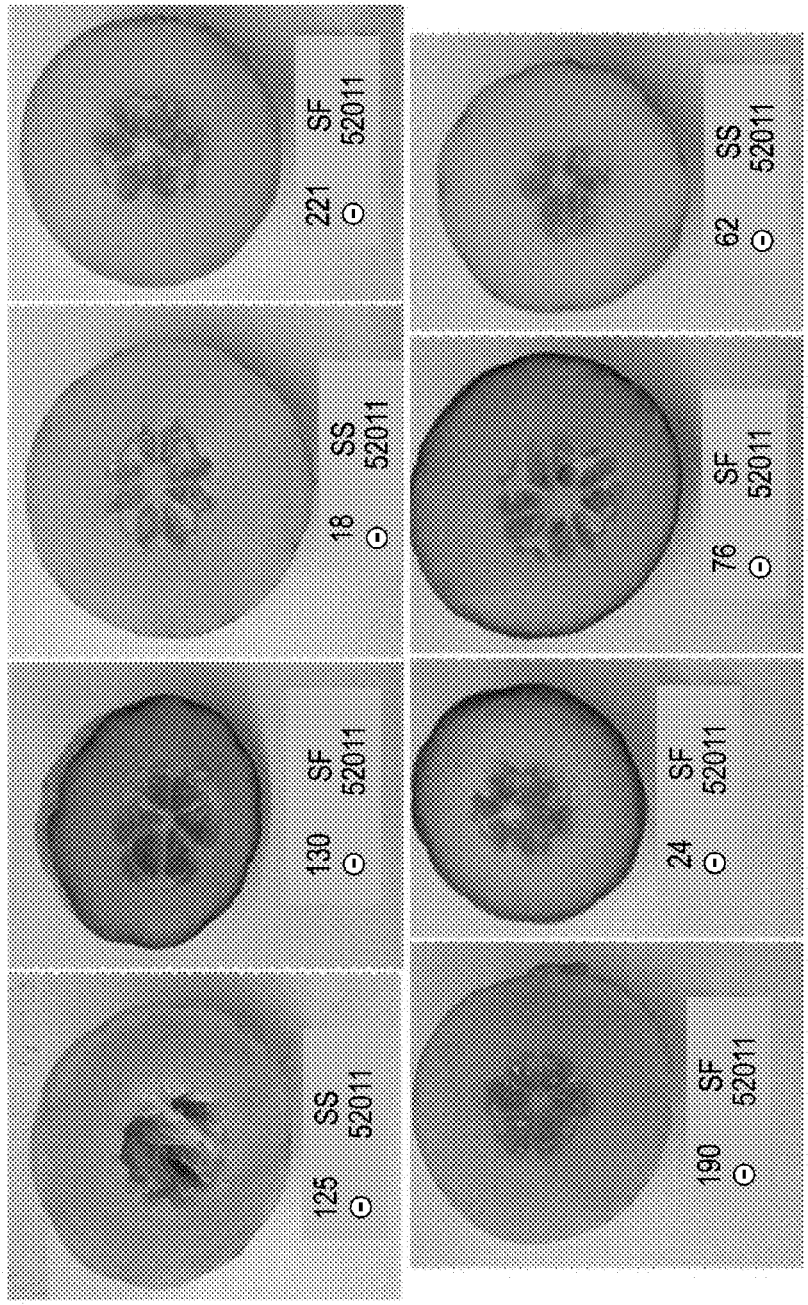
FIG. 2 is a photograph of the interior of various 'sf' fruit types.
Figure 3:
FIG. 3 is a photograph of all the fruit of a representative single 'sf' plant.

Whilst attempting to create novel variations of melon plant, the present inventors treated CEZ (a 'charantais' type melon, developed by ARO) melon seeds with the chemical mutagen ethyl methanesulfonate (EMS) and selected 'super-fruiter' melon plants (referred to herein as "sf" plants) which had enhanced fruit number and yield (FIGS. 1 and 3). Inspection of the fruit from these plants, revealed that their fruit was seedless or had tiny empty undeveloped seeds (FIG. 2). Analysis of carotenoids in the mutated fruit by HPLC revealed similar beta carotene content as compared to the non-mutated isogenic counterpart, CEZ. Furthermore, the total soluble solids (TSS) content revealed that the mutated fruit had a similar sugar content as compared to into non-mutated isogenic counterpart.

Wild type plants of 'CEZ' will develop an average of four fruit per plant and only one fruit will be developed on a branch while the 'sf' is capable of producing multiple fruit on each branch. In wild type plants the successful fertilization of a female flower and the initiation of fruit development will suppress the development of additional fruit from the next female flower on the same branch. This suppression mechanism is inactivated in 'sf'. Reciprocal crosses made with 'sf' indicated that its pollen is fully fertile, fruit will develop only upon fertilization however no seeds or small empty seeds will be contained in the small fruit of 'sf'. Thus 'sf' suffers from seed abortion that does not prevent development of fruit and does not inhibit the production of many additional fruit on the same branch.

This unique yield increase was shown to be governed by a single recessive gene (MELO3C009603, encoding a $Cys_2His_2$ ($C_2H_2$) type zinc finger protein) as demonstrated by segregation analysis of 'sf' in four independent F2 segregating populations.

Thus, according to one aspect of the present invention there is provided a *C. melo* plant or a part thereof, the plant bearing more than 12 fruit, said fruit being seedless.

The term "plant" as used herein encompasses whole plants, ancestors and progeny of the plants and plant parts, including seeds, fruits, shoots, stems, roots (including tubers), and plant cells, tissues and organs. The plant may be in any form including callus tissue, suspension culture, embryos, meristematic regions, leaves, gametophytes, sporophytes, pollen, ovules and microspores.

The term "melon" as used herein refers to the species *Cucumis melo* L. including subspecies *agrestis* (vars. *conomon, makuwa, momordica* and *acidulous*) and *melo* (vars. *cantalupensis, reticulatus, adana, chandalok, ameri, inodorus, flexuosus, chate, tibish, dudaim* and *chito*.

The term "cultivar" is used herein to denote a plant having a biological status other than a "wild" status, which "wild" status indicates the original non-cultivated, or natural state of a plant or accession. The term "cultivar" (for cultivated variety) includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, and advanced/improved cultivar. Examples of cultivars include such cultivated varieties that belong to the taxonomic groups *Cucumis melo* var. *cantalupensis* (the Charantais and Italian cantaloupe fruit types), *Cucumis melo* var. *reticulatis* (the Galia and Ananas fruit types), and *Cucumis melo* var. *inodorus* (including Piel de Sapo, Yellow Canary, Branco and Honeydew fruit types). Therefore, a plant of the present in invention is a plant of any *C. melo* var. The term "var." indicates a varietas (a taxonomic level below that of the species as detailed above).

According to one embodiment, the plant of this aspect of the present invention has an enhanced fruit yield compared to wild-type plants of the same genetic background grown under the same conditions (i.e. bear more than 10 fruit, 12 fruit, 15 fruit, 20 fruit, 25 fruit or even more than 30 fruit at one particular time). Typically, the average weight of each of the fruit is 350 gm with a range of 100-600 gm, depending on the genetic background (FIG. 4B). The plant may comprise at least 2, at least 3, at least 5 fruit per branch at one particular time.

Most of the fruit on the plant are at the same stage of ripening depending on the degree of climacteric/non-climacteric mode of fruit ripening.

It will be appreciated that the weight of total fruit (i.e. crop) of said plant is greater than the weight of total fruit of a wild-type *Cucumis melo* plant.

As used herein the phrase "wild-type *Cucumis melo* plant" refers to the *Cucumis melo* plant having a non-mutated, naturally occurring genome.

The present inventors have shown that the sugar content and the beta carotene content of the melons of the plant of this aspect of the present invention are similar to their non-mutated (wild-type) counterpart. It will be appreciated that the wild-type counterparts do not have a mutation in other genes affecting beta carotene content such as CRTISO, as disclosed in U.S. Patent Application No. 20120324597. Thus, melons of the plant of this aspect of the present invention may be bred to be edible and of high quality in various genetic backgrounds. They are suitable as fresh produce, as fresh cut produce, or for processing such as, for example, canning.

As mentioned, the melons of the plant of this aspect of the present invention are seedless.

As used herein, the term "seedless melon" refers to a melon that does not contain fertilized mature seeds. While the melons of the present invention do not contain fertilized mature seeds, the melons may contain unfertilized ovaries, which are small and white in color. These unfertilized ovaries are not considered to be true seeds. The seed content in the fruit is reduced by at least 80% as compared to that of a wild type melon of the same genetic background and growth conditions.

According to this aspect of the present invention the seedless trait is controlled by a genetic determinant and is independent of exogenous treatment with parthenocarpy-inducing plant hormones. Thus the seedless trait is obtained by stenospermocarpy and not by parthenocarpy.

According to one embodiment, at least 80% of the fruits of a given plant have a seed content reduced by at least 80%, at least 90% to about 99% or even 100%.

According to another embodiment, at least 85% of the fruits of a given plant have a seed content reduced by at least 80%, at least 90% to about 99% or even 100%.

According to another embodiment, at least 90% of the fruits of a given plant have a seed content reduced by at least 80%, at least 90% to about 99% or even 100%.

According to another embodiment, at least 55% of the fruits of a given plant have a seed content reduced by at least 80%, at least 90% to about 99% or even 100%.

According to another embodiment, at least 99% of the fruits of a given plant have a seed content reduced by at least 80%, at least 90% to about 99% or even 100%.

Melon plants of this aspect of the present invention are characterized by having both alleles of the MELO3C009603 gene (wild type cDNA sequence—SEQ ID NO: 7) having a loss of function mutation that results in an enhanced fruit crop trait (and optionally a seedless trait). The MELO3C009603 may have a single mutation which brings about both the traits, or two mutations—one which brings about the enhanced fruit crop trait and the other that brings about the seedless trait. According to a particular embodiment the mutated MELO3C009603 amino acid sequence is set forth in SEQ ID NO: 8.

MELO3C009603 may be in a homozygous form or in a heterozygous form. According to this embodiment, homozygosity is a condition where both alleles at the MELO3C009603 locus are characterized by the same nucleotide sequence. Heterozygosity refers to different conditions of the gene at the MELO3C009603 locus.

The term "allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

The term "gene" as used herein refers to an inherited factor that determines a biological characteristic of an organism (i.e. a melon plant), an "allele" is an individual gene in the gene pair present in the (diploid) melon plant.

A plant is called "homozygous" for a gene when it contains the same alleles of said gene, and "heterozygous" for a gene when it contains two different alleles of said gene. The use of capital letters indicates a dominant (form of a) gene and the use of small letters denotes a recessive gene: "X,X" therefore denotes a homozygote dominant genotype for gene or property X; "X,x" and "x,X" denote heterozygote genotypes; and "x,x" denotes a homozygote recessive genotype. As commonly known, only the homozygote recessive genotype will generally provide the corresponding recessive phenotype (i.e. lead to a plant that shows the property or trait "x") whereas the heterozygotic and homozygote dominant genotypes will generally provide the corresponding dominant phenotype (i.e. lead to a plant that shows the property or trait "X"), unless other genes and/or factors such as multiple alleles, suppressors, codominance etc. (also) play a role in determining the phenotype.

A "loss-of-function mutation" is a mutation in the sequence of a gene, which causes the function of the gene product, usually a protein, to be either reduced or completely absent. A loss-of-function mutation can, for instance, be caused by the truncation of the gene product because of a frameshift or nonsense mutation or by an alteration of a single or more amino acids. A phenotype associated with an allele with a loss of function mutation is usually recessive but can also be dominant.

According to a particular embodiment, both alleles of MELO3C009603 carry an A to T mutation at position 3,450,971 on scaffold 11 of the melon genome, leading to a F/I amino acid change at position 97 of the predicted MELO3C009603 protein. An exemplary polynucleotide sequence of a mutated MELO3C009603 is set forth in SEQ ID NO: 9. An exemplary polypeptide sequence of a mutated MELO3C009603 is set forth in SEQ ID NO: 8.

It will be appreciated that the present invention also contemplates generating the *Cucumis melo* fruit by taking cuttings from 'sf' melon plants and performing vegetative propagation.

Vegetative propagation may be effected using methods well-known in the art, for example in-vitro plant tissue culture, rooting side shoot or protoplast fusion. In one embodiment, a method of vegetatively propagating a plant of the present invention comprises: a) collecting tissue of a plant of the present invention; b) cultivating said tissue to obtain proliferated shoots; c) rooting said proliferated shoots to obtain rooted plantlets; and d) growing plants from said rooted plantlets.

Cuttings according to this aspect of the present invention may include roots, stems, leaves, cotyledons, flowers, fruit, embryos and pollen. Preferably, the cuttings comprise stems and epical or side shoot meristem.

According to one embodiment, the plants of the present invention are of a hybrid variety—i.e. are generated following the crossing (i.e. mating) of two non-isogenic plants. The hybrid may be an $F_1$ Hybrid or an open-pollinated variety.

An $F_1$ Hybrid" as used herein, refers to first generation progeny of the cross of two non-isogenic plants.

The development of melon hybrids of the present invention requires the development of stable parental lines while at least one of them is heterozygous to sf gene. In breeding programs desirable traits from two or more germplasm sources or gene pools are combined to develop superior breeding varieties. Desirable inbred or parent lines are developed by continuous self-pollinations and selection of the best breeding lines, sometimes utilizing molecular markers to speed up the selection process.

Once the parental lines that give the best hybrid performance have been identified e.g., both carrying the mutation in the MELO3C009603, the hybrid seed can be produced indefinitely, as long as the homogeneity of the parents are maintained. According to one embodiment the melon plants of the present invention are stable parent plant lines (carrying a loss of function mutation in the MELO3C009603 gene in a heterozygous form).

As defined herein, the phrase "stable parental lines" refers to open pollinated, inbred lines, stable for the desired plants over cycles of self-pollination and planting. Typically, 95% of the genome is in a homozygous form in the parental lines of the present invention.

According to another aspect, the present invention provides a method for producing first generation ($F_1$) 'sf' hybrid melon plantlets.

According to one embodiment, the present invention provides a method for producing first generation 'sf' hybrid plantlets (and also seeds) comprising crossing (e.g. pollinating) a first stable parent melon plant which is seedless and has an enhanced fruit crop (e.g. either homozygote or heterozygote for the mutation MELO3C009603) with a second stable 'sf' heterozygous parent melon plant.

It will be appreciated that 25 or 50% of the $F_1$ hybrid melon seeds are homozygous for a MELO3C009603 mutation, depending if only one or both parental lines are heterozygous 'sf'.

According to another embodiment, the present invention also provides a DNA marker that enables selecting the $F_1$ 'sf' plantlets.

Thus, according to another aspect of the present invention, there is provided a *Cucumis melo* plant having a MELO3C009603/melo3c009603 genome such that upon selfing 25% of F1 bear more than 5 fruit, said fruit being seedless.

The present invention also relates to seeds harvested from these $F_1$ hybrid melon plants and plants grown from these seeds.

A common practice in plant breeding is using the method of backcrossing to develop new varieties by single trait conversion.

The phrase "single trait conversion" as used herein refers to the incorporation of new single gene into a parent line wherein essentially all of the desired morphological and physiological characteristics of the parent lines are recovered in addition to the single gene transferred.

The term "backcrossing" as used herein refers to the repeated crossing of a hybrid progeny back to one of the parental melon plants. The parental melon plant which contributes the gene for the desired characteristic is termed the non-recurrent or donor parent. This terminology refers to the fact that the non-recurrent parent is used one time in the backcross protocol and therefore does not recur. The parental melon plant to which the gene from the non-recurrent parent are transferred is known as the recurrent parent as it is used for several rounds in the backcrossing protocol.

In a typical backcross protocol, a plant from the original varieties of interest (recurrent parent) is crossed to a plant selected from second varieties (non-recurrent parent) that carries the single gene of interest to be transferred. The resulting progeny from this cross are then crossed again to the recurrent parent and the process is repeated until a melon plant is obtained wherein essentially all of the desired morphological and physiological characteristics of the recurrent parent are recovered in the converted plant, in addition to the single transferred gene from the non-recurrent parent.

Thus, near-isogenic lines (NIL) may be created by many backcrosses to produce an array of individuals that are nearly identical in genetic composition except for the trait or genomic region under interrogation in this case 'sf' mutation in MELO3C009603.

Backcrossing methods can be used with the present invention to improve or introduce a characteristic into the parent lines.

Marker assisted selection of *C. melo* plantlets that will bear more than 5 seedless fruit (or parts thereof that are capable of producing a plant that bears more than 5 seedless fruit) may be performed. This is especially advantageous for selecting cuttings or during a backcrossing process. The method comprises analyzing for the presence of the A/T mutation that leads to F/I amino acid change at position 97 of MELO3C009603 predicted protein, wherein the presence of the mutation is indicative that the plant will bear more than 5 seedless fruit or the part thereof will produce a plant that bears more than 5 seedless fruit.

Many methods are known in the art for analyzing for mutations including for example single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, Flap Endonuclease-mediated assays, restriction fragment length polymorphism (RFLP), electrophoresis, sequence alignment, allelic specific oligonucleotide hybridization (ASO) and random amplified polymorphic DNA (RAPD).

Thus, the present invention contemplates oligonucleotides (e.g. Primers) that can be used to distinguish between the mutated and non-mutated form of MELO3C009603. An exemplary set of primers is described in the Example section—SEQ ID NOs: 3 and 4.

The present inventors contemplate both chemical mutagenesis and recombinant techniques for the generation of the melon plants of the present invention.

Thus, the melon plants of the present invention may be generated by exposing the melon plant or part thereof to a chemical mutagen. Examples of chemical mutagens include, but are not limited to nitrous acid, alkylating agents such as ethyl methanesulfonate (EMS), methyl methane sulfonate (MMS), diethylsulfate (DES), and base analogs such as 5-bromo-deoxyuridine (5BU). An exemplary method for generating the melon plants of the present invention using chemical mutagenesis includes soaking melon seeds for 12 hours in water followed by additional 12 hours in EMS (e.g. 1%). The treated seeds ($M_1$) are then planted and self pollinated to prepare $M_2$ families.

As mentioned, the melon plant of the present invention may also be generated using other techniques including but not limited to (a) deletion of the MELO3C009603 gene; (b) transcriptional inactivation of the MELO3C009603 gene (c) antisense RNA mediated inactivation of transcripts of the MELO3C009603 gene; (d) translational inactivation of transcripts of the MELO3C009603 gene; and (e) genome editing of MELO3C009603 gene.

Thus, for example, gene knock-in or gene knock-out constructs including sequences homologous with the MELO3C009603 gene can be generated and used to insert an ancillary sequence into the coding sequence of the enzyme encoding gene, to thereby inactivate this gene.

These construct preferably include positive and negative selection markers and may therefore be employed for selecting for homologous recombination events. One ordinarily skilled in the art can readily design a knock-in/knock-out construct including both positive and negative selection genes for efficiently selecting transformed plant cells that underwent a homologous recombination event with the construct. Such cells can then be grown into full plants. Standard methods known in the art can be used for implementing knock-in/knock out procedure. Such methods are set forth in, for example, U.S. Pat. Nos. 5,487,992, 5,464, 764, 5,387,742, 5,360,735, 5,347,075, 5,298,422, 5,288,846, 5,221,778, 5,175,385, 5,175,384, 5,175,383, 4,736,866 as well as Burke and Olson, Methods in Enzymology, 194: 251-270, 1991; Capecchi, Science 244:1288-1292, 1989; Davies et al., Nucleic Acids Research, 20 (11) 2693-2698, 1992; Dickinson et al., Human Molecular Genetics, 2(8): 1299-1302, 1993; Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742-750 1991; Jakobovits et al., Nature, 362:255-261 1993; Lamb et al., Nature Genetics, 5: 22-29, 1993; Pearson and Choi, Proc. Natl. Acad. Sci. USA, 1993, 90:10578-82; Rothstein, Methods in Enzymology, 194:281-301, 1991; Schedl et al., Nature, 362: 258-261, 1993; Strauss et al., Science, 259:1904-1907, 1993, WO 94/23049, WO93/14200, WO 94/06908 and WO 94/28123 also provide information.

Thus according to a particular embodiment of the present invention, the melon plant is generated by introduction thereto of a nucleic acid construct, the nucleic acid construct comprising a nucleic acid sequence encoding a polynucleotide agent which up-regulates an expression of MELO3C009603 having a mutation which brings about an enhanced crop yield trait (and optionally a seedless trait) and a cis-acting regulatory element capable of directing an expression of the polynucleotide agent in the plant.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. The genetic construct can be an expression vector wherein the nucleic acid sequence is operably linked to one or more regulatory sequences allowing expression in the plant cells.

The polynucleotide according to this aspect of the present invention may encode MELO3C009603 having for example an F/I mutation at position 97. The polypeptide sequence of an exemplary MELO3C009603 having an a F/I mutation at position 97 is typically at least 90% homologous, at least 91% homologous, at least 92% homologous, at least 93% homologous, at least 94% homologous, at least 95% homologous, at least 96% homologous, at least 97% homologous, at least 98% homologous, at least 99% homologous, or 100% homologous to the sequence set forth in SEQ ID NO: 8. The nucleic acid sequence of an exemplary polynucleotide which encodes such a protein may be at least 90% homologous, at least 91% homologous, at least 92% homologous, at least 93% homologous, at least 94% homologous, at least 95% homologous, at least 96% homologous, at least 97% homologous, at least 98% homologous, at least 99% homologous, or 100% homologous to the nucleic acid sequence set forth in SEQ ID NO: 9.

In a particular embodiment of the present invention the regulatory sequence is a plant-expressible promoter.

As used herein the phrase "plant-expressible" refers to a promoter sequence, including any additional regulatory elements added thereto or contained therein, is at least capable of inducing, conferring, activating or enhancing expression in a melon cell, tissue or organ.

The promoter may be a regulatable promoter, a constitutive promoter or a tissue-associated promoter.

As used herein, the term "regulatable promoter" refers to any promoter whose activity is affected by specific environmental or developmental conditions.

As used herein, the term "constitutive promoter" refers to any promoter that directs RNA production in many or all tissues of a plant transformant at most times.

As used herein, the term "tissue-associated promoter" refers to any promoter which directs RNA synthesis at higher levels in particular types of cells and tissues (e.g., a fruit-associated promoter).

Exemplary promoters that can be used to express an operably linked nucleic acid sequence (i.e. transgene) include the cauliflower mosaic virus promoter, CaMV and the tobacco mosaic virus, TMV, promoter.

Other promoters that can be used in the context of the present invention include those described in U.S. Patent No. 20060168699 and by Hector G. Numez-Palenius et al. [Critical Reviews in Biotechnology, Volume 28, Issue 1 Mar. 2008, pages 13-55], both of which are incorporated herein by reference.

Plant cells may be transformed stably or transiently with the nucleic acid constructs of the present invention. In stable transformation, the nucleic acid molecule of the present invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND METHODS

Plant Material

Seeds of 'CEZ', a 'Charentais' type melon (*Cucumis melo* subsp. *melo* Cantalupensis Group), were subjected to EMS mutagenesis, $M_1$ plants were self-pollinated, $M_2$ families were visually phenotyped and mutant lines were selected as described previously (Tadmor et al., 2007). Plants were grown under conventional conditions in the field and in the greenhouse.

Fruit Carotenoid Analysis

Five mature fruit were harvested, peeled, sliced and a central slice was cut into small cubes and immediately frozen in liquid nitrogen. Frozen fruit samples were ground to a fine powder by A11 analytical grinding mill (Ika) in the presence of liquid nitrogen. Carotenoids were extracted from 0.5 g ground tissue in hexane:acetone:ethanol (50:25:25, v/v/v) mixture as described in Tadmor et al., (2005) and were analyzed, identified, and quantified with a Waters (Milford, Mass.) 2695 HPLC apparatus equipped with a Waters 996 PDA detector and Millennium software (Waters), as described previously (Tadmor et al., 2000).

RNA Extraction

RNA extraction for RNA-seq analysis was performed according to Portnoy et al 2011, as described below. Additional RNA extraction for RT-PCR used the same protocol, downscaled by 1/20, starting with about 100 mg frozen tissue in 1.5 ml tubes.

Frozen fruit rind tissues (about 5 g of 1.5 mm wide fruit rind) were pulverized with a mortar and pestle in liquid nitrogen. Pulverized tissue was mixed well by vortexing in a 50 mL tube with 10 mL of extraction buffer containing 0.2M Tris-HCl (pH 9.0), 0.2M ethylenediaminetetraacetic acid (EDTA), 0.4M NaCl, and 2% (w/v) SDS, and incubated at 65° C. for 5 min. Then 30% (w/v) sodium lauroylsarcosine was added to a final concentration of 2% (v/v), and the mixture was vortexed and incubated at 65° C. for 2 to 3 min. An equal volume of phenol was added to the solution, vortexed, and centrifuged at 5000 g for 5 min. The aqueous phase was transferred to a new 50 mL tube on ice, following three rounds of chloroform-isoamyl alcohol (24:1, v/v) extractions. Nucleic acids were precipitated with 1/10 volume of 3M sodium acetate (NaAc) (pH 5.3) and 2 volumes of 95% (v/v) EtOH. The resulting nucleic acid pellet was dissolved in 10 mL 2M LiCl at 4° C. overnight. Total RNA was precipitated by centrifugation at 15,000 g for 10 min at 4° C. and dissolved in 0.5 mL diethylpyrocarbonate (DEPC) water. After reprecipitation with 1/10 volume of 3M NaAc (pH 5.3) and 2 volumes of 95% EtOH, the pellet was dissolved in 50 to 100 µL DEPC water. RNA was further treated with DNase I (Thermo scientific) according to the manufacturer's protocol. After DNase reaction, samples were cleaned by chloroform-isoamyl alcohol extraction, precipitated with 1/10 volume of 3M NaAc and 2 volumes of 95% EtOH, cleaned with 70% EtOH, air dried for 5 min and diluted in water. The quality of the RNA was analyzed by ND-1000 spectrophotometer (NanoDrop Technologies, Wilmington, Del.), electrophoresis in SB 1% Agarose gel, and PCR of intron flanking primers to check if presence of DNA contamination is observed on Agarose gel.

Leaf RNA was extracted with triReagent (Sigma), according to manufacturer's instructions. DNaseI (Thermo scientific) was applied according to manufacturer's protocol, and cleaned by the addition of chloroform-isoamyl alcohol, precipitated with Isopropanol, washed with 70% EtOH, left for 5 minutes to air dry and dissolved in ddH2O. Concentration of RNA was determined by NanoDrop.

RNA-Seq

After DNase treatment RNA samples were checked for integrity on a 1% Agarose gel, checked for purity in Nano-Drop (260/280 ratio of around 2, 260/230 of around 2.4), and absence of DNA contamination was determined by PCR analysis with EF1α-intron primers.

SEQ ID NO: 1
F-AGGCTGATTGTGCTGTCCTT;

SEQ ID NO: 2
R-GATGGGAACGAAGGGAATTT.

Samples containing DNA contamination should yield amplicons of 391 bp, in contrast to 303 bp cDNA, when fractionated on an Agarose gel. Samples containing about 30 µg RNA were precipitated with two volumes of EtOH and 1/10 volume of 3M NaAc and stored at (−20° C.). Construction of strand-specific libraries was performed with TruSec RNA S amp Prep Kit FC-121-1031 (Illumina Inc) according to the manufacturer's instructions. Twelve libraries were shipped on dry ice for sequencing with the Illumina HiSeq2000. Each library was individually barcoded and all libraries were sequenced in one Illumina lane yielding and average of $17 \times 10^6$ reads of 50 bp per library. The Illumina reads were sorted to their libraries and barcodes were removed. Raw reads were trimmed for low quality bases at the end of the RNA-seq and low-quality reads were removed using the FASTX-toolkit. The resulting high quality reads were then mapped to the melon genome using TopHat version v2.0.10 (Kim et al., 2011) and were counted using HTseq v0.5.3p3. Bioconductor DESeq package (Anders, 2010) in the R environment was used to identify differentially expressed genes between 'sf' and 'wildtype' samples. Genes showing FDR<0.05 were considered as differential expressed. SNP analysis was carried using the variant calling routines GATK Unified Genotyper program (version 2.5-2) (DePristo et al., 2011) and filtered to achieve a high-confidence SNP set.

RT-PCR

1 µg of RNA was used for cDNA synthesis using 'Verso system' (Thermo Scientific) according to the manufacturer's instructions. Reaction was performed in an Eco RT-PCR system (Illumina). Each sample contained: 1 µl cDNA, 0.2 µl of each primer (10 mM), 5 µl of FastSYBR green master mix reaction mix (Applied Biosystems) and 3.6 µl ddH2O. The machine was programmed as specified by the enzyme manufacturer. Each analysis was conducted in relation to the housekeeping gene ARP1, and analyzed in Eco version 4 software.

DNA Extraction

Young plant meristems (about 1 gr) were ground in liquid nitrogen with mortar and pestle. DNA extraction solution was prepared by mixing extraction buffer (0.35 M Sorbitol, 0.1 M Tris, 5 mM EDTA, pH7, add 0.02 M NaBisulfite before use): nucleic lysis buffer (0.35 M Sorbitol, 0.1 M Tris, 5 mM EDTA, pH7, add 2% CTAB before use): 5% sarkosyl, in ratio of 1:1:0.4. All chemicals were supplied by Sigma. DNA extraction solution was incubated in 65° C. 600 µl DNA extraction solution were added to 100 µg tissue weighted into 1.5 ml tube, mixed and incubated in 65° C. for 10 minutes. 600 µl chloroform:isoamylalcohol (ratio 24:1) were added, mixed for 5 minutes in 200 RPM, centrifuged at 15,000 g for 10 minutes and supernatant was removed into a new tube. Cold isopropanol (⅔ of supernatant volume) was added, mixed, incubated for 30 minutes to over-night in (−20° C.), centrifuged at 20,000 g for 10 minutes, liquid phase removed, pellet washed with 70% EtOH, precipitated again and EtOH was removed, pellet air dried for 5 minutes, dissolved with 50-200 µl water, 2 µl RNase were added, samples were incubated at 37° C. for 30 min, centrifuged at 15,000 g for 3 min and supernatant was removed to a new tube. Concentration and purity of DNA were determined in NanoDrop, integrity of DNA was checked on a 0.8% Agarose gel.

RESULTS

Identification of Superfruiter

Visual phenotyping of 2,000 M$_2$ families derived from mutagenized seeds of the breeding line 'CEZ' was performed. Each M$_2$ family was represented in the field by 12 plants. One family segregated for a unique phenotype; 3 out of the 12 plants grown in the field carried more than 15 fruit per plant (FIGS. 1 and 2) as compared to the wild type plants which carried on average 3 fruit. Each of the mutants' fruit weighed around 300 gr while the wild type fruit weighed about 900 gr. Interestingly, the mutant's fruit had no seeds or very tiny empty seeds. This mutation is referred to herein as 'superfruiter' (FIG. 3). When the fruit of a 'sf' plant was diluted, the fruit remained small.

Inheritance of Super Fruiter

Cuttings of superfruiter ('sf') plants were transferred to the greenhouse once they developed sufficient roots. The 'sf' plants developed from the cuttings could not be self-pollinated. However their pollen was used for successful pollination of 'CEZ', 'Noy Yizre'el', 'Ein Dor' and 'Piel De Sapo' lines and viable F$_1$ seeds were obtained. These seeds were planted and F$_1$ plants were successfully self-pollinated to yield F$_2$ seeds. 150-200 plants of each of the F$_2$ populations were planted in the field, allowed to grow under commercial production conditions and were open pollinated by bees. Once fruit was generated the present inventors could visually distinguish between 'sf' and wild type phenotypes. In all four F$_2$ populations 'sf' segregated as a single recessive gene (Table 1)

TABLE 1

| F$_2$ population | n | phenotype | Observed | Expected | Chi square | P value |
| --- | --- | --- | --- | --- | --- | --- |
| ED x sf | 188 | sf | 43 | 47 | 0.454 | 0.5005 |
|  |  | WT | 145 | 141 |  |  |
| NY x sf | 166 | sf | 39 | 41.5 | 0.201 | 0.6541 |
|  |  | WT | 127 | 124.5 |  |  |
| CEZ x sf | 191 | sf | 48 | 47.75 | 0.002 | 0.9667 |
|  |  | WT | 143 | 143.25 |  |  |
| PDS x sf | 194 | sf | 38 | 48.5 | 3.031 | 0.0817 |
|  |  | WT | 156 | 145.5 |  |  |

Chi square value of the deviation of segregants from the 1:3 expected Mendelian ratio.
'n'—population size;
P value that is larger than 0.05 indicates that there is a high probability that the observed deviations could be due to random chance alone.

To estimate the yield of 'sf' the present inventors measured the fruit number and weight of all 'sf' plants, divided the sum of fruit by plant number to obtain a mean fruit number per plant, divided the sum of fruit weight by plant number to obtain a mean yield per plant and divided the sum of fruit weight by fruit number to obtain a mean fruit weight. Similar measurements and calculations were conducted for wild type plants. In all tested genetic backgrounds 'sf' carried significantly more fruit (FIG. 4A), significantly smaller fruit (FIG. 4B) and significantly higher yield per plant (FIG. 4C).

To determine the effect of 'sf' on fruit quality the present inventors randomly picked 10 mature fruit of CEZ and of CEZx'sf wildtype and 'sf' phenotype segregants. Fruit were tasted, analyzed for total soluble solids (TSS) as an index for sugar content, HPLC analyzed for β-carotene content. No effect of 'sf' on melon fruit flavor that is mainly determined by sugar content was detected. No quality difference between 'sf', wild type segregants or 'CEZ' was detected including TSS or β-carotene content (FIGS. 5A-B).

To identify the gene that determines 'sf' phenotype, two replications of 10 plants showing either 'sf' or wild type phenotype in the 'sf' X NY and in the 'sf' X ED segregating F$_2$ populations, 'sf' phenotype from the 'sf' X CEZ segregating F$_2$ population and the 'sf' originator line, CEZ were selected. From each of these plants shoot meristems, stems, female flowers and young fruit at the age of 2-4 days after pollination were sampled. RNA was extracted from bulks of each tissue x phenotype combination. Equal amounts of RNA from all tissues were combined to develop two replications of 'sf' and wild type phenotypes of 'sf' X NY and of 'sf' X ED segregating F$_2$ populations (eight pools), 'sf' phenotype from the 'sf' X CEZ segregating F$_2$ population and the 'sf' originator line, CEZ (four pools). Twelve libraries were RNA-Seq analyzed with Illumina HiSeq 2000 yielding an average of $17 \times 10^6$ reads for each library. Single Nucleotide Polymorphism (SNP) identified by comparing RNA-Seq data of phenotypic pools, derived from 'sf' X NY and of 'sf' X ED segregating F$_2$ populations, were scattered along the melon genome however most of them were located on scaffold 11. The present inventors then looked for SNP that were homozygous in 'CEZ', carried the alternative allele in all 'sf phenotypes' and carried mostly 'CEZ' allele in all wild type phenotypes. A single SNP in MELO3C009603 that is located on scaffold 11 of chromosome 4 was fixed in all 'sf' material ('A') compared to 'CEZ' ('T') and was the minor allele in all 'wild type' phenotypes.

Primers were designed that PCR amplify a 213 bp fragment that has an ApoI restriction site in the wild type allele that is mutated in sf.

SEQ ID NO: 3
F TAGACATGAGCCGCATCTGA

SEQ ID NO: 4
R GAACGTGGCAACAACAACAA

Conducting an ApoI digestion on the PCR amplified fragment yields a 140 bp and a 73 bp fragments in wild type, a 213 bp fragment when a homozygote 'sf' mutant is digested and all three bands in the heterozygote (FIG. 6). This marker showed complete co-segregation with 'sf' phenotype in four independent F$_2$ populations consisting of at least 300 plants each.

MELO3C009603 codes for a Cys$_2$ His$_2$ Zinc Finger (ZF) protein. The 'T' to 'A' transversion changed TTC, which codes for the highly conserved amino acid phenylalanine at position 97 ($F^{97}$), to ATC that codes for isoleucine (I) in the ZF motif (FIG. 7).

RNA-Seq data indicated that the digital expression of MELO3C009603 is low, only 40-60 reads in each bulk, and similar in both bulks. These bulks included a mix of several tissues. The relative expression of MELO3C009603 in each of these tissues using quantitative RTPCR was analyzed and it was found that it has similar low expression in leaves and similar very low expression in all other analyzed tissues (FIGS. 8A-B).

Analysis of RNA-Seq data for differentially expressed genes (DEG) identified 103 genes that showed more than two fold change between 'CEZ' and 'sf', the isogenic comparison. Only 55 genes, out of these 103, showed significant difference while using the adjusted P value out of these 55 only 14 genes showed significant differential expression between 'sf' and 'wild type' bulks in all three analyzed segregating populations (FIG. 9 and Table 2, herein below). Of these 14 genes only MELO3C021150 that codes for a seed nucellus-specific protein homolog was down regulated in 'sf' of all three analyzed population and MELO3C003230, which codes for a putative anthocyanin 5-aromatic acyltransferase homolog, was up regulated in 'sf' of the analyzed populations. The other twelve genes show similar direction of change in 'CEZ x sf' and in 'ED x sf' but opposite direction in 'NY x sf' $F_2$ population (Table 2, herein below). Quantitative RT-PCR analysis of MELO3C021150 in different organs indicated that the digital expression found between the bulks is contributed by the young fruit tissue and that MELO3C021150 is not transcribed in all other tissues (FIG. 10B).

TABLE 2

| C | Sub-C | ID | CEZ sf | CEZ WT | WT/sf | P | Adj P | ED sf | ED WT | WT/sf | P | Adj P | NY sf | NY WT | WT/sf | P | Adj P | ACC | DESC |
|---|---|---|---|---|---|---|---|---|---|---|---|---|---|---|---|---|---|---|---|
| 1 | AAA | MELO3C021150 | 2.5 | 139.5 | 56.5 | 0.0000 | 0.0000 | 1.9 | 20.4 | 10.6 | 0.0001 | 0.0130 | 1.1 | 36.8 | 32.2 | 0.0000 | 0.0000 | AAB82329 | seed nucellus-specific protein [Citrullus lanatus] |
| 1 | AAA | MELO3C003230 | 953.6 | 331.1 | 0.3 | 0.0000 | 0.0009 | 953.6 | 253.4 | 0.4 | 0.0000 | 0.0003 | 1,277.1 | 346.0 | 0.3 | 0.0000 | 0.0002 | XP_002531355 | Anthocyanin 5-aromatic acyltransferase, putative [Ricinus communis] |
| 2 | AA | MELO3C022716 | 3.9 | 247.2 | 63.4 | 0.0000 | 0.0000 | 1.4 | 7.8 | 5.6 | 0.0486 | 1.0000 | 5.2 | 46.9 | 9.0 | 0.0000 | 0.0003 | AAB82329 | seed nucellus-specific protein [Citrullus lanatus] |
| 2 | AA | MELO3C023027 | 2,064.6 | 401.0 | 0.2 | 0.0000 | 0.0000 | 2,064.6 | 668.2 | 0.5 | 0.0001 | 0.0239 | 821.0 | 437.8 | 0.5 | 0.0152 | 0.4081 | AAM74923 | 17 kDa phloem lectin Lec17-1 [Cucumis melo] |
| 2 | AA | MELO3C015490 | 170.1 | 35.7 | 0.2 | 0.0000 | 0.0000 | 170.1 | 59.1 | 0.6 | 0.0486 | 1.0000 | 256.8 | 80.2 | 0.3 | 0.0001 | 0.0059 | XP_002514129 | calmodulin binding protein, putative [Ricinus communis] |
| 2 | AA | MELO3C027040 | 1,176.0 | 352.7 | 0.3 | 0.0000 | 0.0001 | 1,176.0 | 363.7 | 0.3 | 0.0000 | 0.0000 | 559.6 | 333.6 | 0.6 | 0.0500 | 0.8348 | AAM74923 | 17 kDa phloem lectin Lec17-1 [Cucumis melo] |
| 2 | AA | MELO3C024762 | 365.0 | 111.0 | 0.3 | 0.0000 | 0.0004 | 365.0 | 70.4 | 0.3 | 0.0000 | 0.0010 | 176.8 | 80.6 | 0.5 | 0.0064 | 0.2300 | AAW51125 | putative alcohol acyl-transferases [Cucumis melo] |
| 2 | AA | MELO3C007337 | 54.3 | 10.5 | 0.2 | 0.0000 | 0.0017 | 54.3 | 25.7 | 0.5 | 0.0187 | 0.7167 | 132.5 | 45.1 | 0.3 | 0.0006 | 0.0374 | ADL36665 | COL domain class transcription |

TABLE 2-continued

| C | Sub-C | ID | CEZ sf | CEZ WT | WT/sf | P | Adj P | ED sf | ED WT | WT/sf | P | Adj P | NY sf | NY WT | WT/sf | P | Adj P | ACC | DESC |
|---|---|---|---|---|---|---|---|---|---|---|---|---|---|---|---|---|---|---|---|
| 2 | AA | MELO3C006043 | 468.3 | 167.9 | 0.4 | 0.0000 | 0.0024 | 468.3 | 235.6 | 0.6 | 0.0062 | 0.3771 | 695.8 | 250.4 | 0.4 | 0.0002 | 0.0140 | ADN34176 | factor [*Malus × domestica*] UDP-glucose:glucosyltransferase [*Cucumis melo* subsp. *melo*] |
| 2 | AA | MELO3C026488 | 468.8 | 198.2 | 0.4 | 0.0004 | 0.0201 | 468.8 | 113.2 | 0.4 | 0.0002 | 0.0299 | 401.8 | 191.0 | 0.5 | 0.0068 | 0.2404 | O49858 | RecName: Full = Cytochrome P45082A3; AltName: Full = Cytochrome P450CP6 |
| 2 | A | MELO3C002560 | 452.8 | 66.6 | 0.1 | 0.0000 | 0.0000 | 452.8 | 59.1 | 0.6 | 0.0372 | 1.0000 | 151.3 | 92.8 | 0.6 | 0.0966 | 1.0000 | AAY85179 | fiber expressed protein [*Gossypium hirsutum*] |
| 2 | A | MELO3C007961 | 17.9 | 127.3 | 7.1 | 0.0000 | 0.0000 | 17.9 | 36.7 | 3.3 | 0.0010 | 0.1077 | 9.9 | 16.1 | 1.6 | 0.3521 | 1.0000 | BAB40817 | endochitinase MCHT-2 [*Cucumis melo*] |
| 2 | A | MELO3C008466 | 167.9 | 32.1 | 0.2 | 0.0000 | 0.0000 | 167.9 | 9.9 | 0.4 | 0.0304 | 0.9321 | 42.3 | 18.7 | 0.4 | 0.0363 | 0.6980 | XP_002520298 | calcium binding protein/cast, putative [*Ricinus communis*] |
| 2 | A | MELO3C013917 | 206.2 | 53.5 | 0.3 | 0.0000 | 0.0001 | 206.2 | 56.2 | 0.6 | 0.0296 | 0.9195 | 248.0 | 102.3 | 0.4 | 0.0021 | 0.0950 | ADE41101 | AP2 domain class transcription factor [*Malus × domestica*] |
| 2 | A | MELO3C023255 | 66.5 | 13.8 | 0.2 | 0.0000 | 0.0008 | 66.5 | 43.3 | 0.6 | 0.0665 | 1.0000 | 66.7 | 32.9 | 0.5 | 0.0358 | 0.6926 | XP_002328473 | predicted protein [*Populus trichocarpa*] |
| 2 | A | MELO3C005711 | 353.7 | 125.2 | 0.4 | 0.0000 | 0.0031 | 353.7 | 181.9 | 0.5 | 0.0017 | 0.1555 | 606.4 | 293.8 | 0.5 | 0.0075 | 0.2576 | XP_002509857 | metal ion binding protein, putative [*Ricinus communis*] |
| 2 | A | MELO3C011268 | 8.5 | 38.2 | 4.5 | 0.0003 | 0.0176 | 8.5 | 43.2 | 1.9 | 0.0380 | 1.0000 | 5.1 | 19.5 | 3.8 | 0.0173 | 0.4476 | XP_002515504 | ATP binding |

TABLE 2-continued

| C | Sub-C | ID | CEZ sf | CEZ WT | CEZ WT/sf | P | Adj P | ED sf | ED WT | ED WT/sf | P | Adj P | NY sf | NY WT | NY WT/sf | P | Adj P | ACC | DESC |
|---|---|---|---|---|---|---|---|---|---|---|---|---|---|---|---|---|---|---|---|
| 2 | A | MELO3C021821 | 198.7 | 77.7 | 0.4 | 0.0004 | 0.0233 | 198.7 | 187.6 | 1.7 | 0.0236 | 0.8141 | 257.9 | 127.4 | 0.5 | 0.0127 | 0.3633 | XP_002328950 | protein, putative [Ricinus communis] |
| 2 | A | MELO3C026807 | 102.0 | 37.3 | 0.4 | 0.0007 | 0.0331 | 102.0 | 30.1 | 0.5 | 0.0412 | 1.0000 | 2.2 | 1.3 | 0.6 | 0.8120 | 1.0000 | | glycosyl-transferase, CAZy family GT2 [Populus trichocarpa] |
| 1 | BBB | MELO3C003917 | 924.3 | 42.2 | 0.0 | 0.0000 | 0.0000 | 924.3 | 14.1 | 0.0 | 0.0000 | 0.0000 | 60.4 | 3,450.8 | 57.1 | 0.0000 | 0.0000 | ACC93947 | heat-shock protein 70 [Hevea brasiliensis] |
| 1 | BBB | MELO3C027124 | 853.0 | 41.8 | 0.0 | 0.0000 | 0.0000 | 853.0 | 9.5 | 0.1 | 0.0000 | 0.0000 | 40.4 | 3,290.9 | 81.4 | 0.0000 | 0.0000 | ADM47405 | small molecular heat shock protein [Nicotiana tabacum] |
| 1 | BBB | MELO3C025139 | 1,852.7 | 189.9 | 0.1 | 0.0000 | 0.0000 | 1,852.7 | 157.4 | 0.4 | 0.0000 | 0.0013 | 223.6 | 5,792.0 | 25.9 | 0.0000 | 0.0000 | ADM47405 | small molecular heat shock protein [Nicotiana tabacum] |
| 1 | BBB | MELO3C021172 | 4,697.3 | 673.7 | 0.1 | 0.0000 | 0.0000 | 4,697.3 | 1,160.9 | 0.5 | 0.0002 | 0.0315 | 1,599.9 | 3,878.2 | 2.4 | 0.0007 | 0.0430 | XP_002880227 | BCL-2-associated athanogene 6 [Arabidopsis lyrata subsp. lyrata] |
| 1 | BBB | MELO3C002020 | 5,756.5 | 1,131.6 | 0.2 | 0.0000 | 0.0000 | 5,756.5 | 206.6 | 0.4 | 0.0000 | 0.0032 | 337.1 | 1,608.5 | 4.8 | 0.0000 | 0.0000 | AAX08108 | heat shock protein 101 [Vitis vinifera] |
| 1 | BBB | MELO3C026374 | 857.8 | 157.0 | 0.2 | 0.0000 | 0.0000 | 857.8 | 48.3 | 0.4 | 0.0003 | 0.0391 | 73.0 | 585.7 | 8.0 | 0.0000 | 0.0000 | ADM47405 | small molecular heat shock protein [Nicotiana tabacum] |
| 1 | BBB | MELO3C006933 | 252.0 | 37.4 | 0.1 | 0.0000 | 0.0000 | 252.0 | 1.7 | 0.1 | 0.0001 | 0.0192 | 11.6 | 88.8 | 7.7 | 0.0000 | 0.0000 | XP_002318188 | predicted protein [Populus trichocarpa] |

TABLE 2-continued

| C | Sub-C | ID | CEZ sf | CEZ WT | WT/ sf | P | Adj P | ED sf | ED WT | WT/ sf | P | Adj P | NY sf | NY WT | WT/ sf | P | Adj P | ACC | DESC |
|---|---|---|---|---|---|---|---|---|---|---|---|---|---|---|---|---|---|---|---|
| 1 | BBB | MELO3C003195 | 107.3 | 16.5 | 0.2 | 0.0000 | 0.0000 | 107.3 | 6.1 | 0.0 | 0.0000 | 0.0000 | 13.4 | 57.2 | 4.3 | 0.0002 | 0.0179 | XP_002534180 | heat-shock protein, putative [*Ricinus communis*] |
| 1 | BBB | MELO3C006935 | 9,853.8 | 2,844.1 | 0.3 | 0.0000 | 0.0000 | 9,853.8 | 186.1 | 0.4 | 0.0001 | 0.0180 | 325.9 | 3,182.2 | 9.8 | 0.0000 | 0.0000 | XP_002513649 | heat shock protein, putative [*Ricinus communis*] |
| 1 | BBB | MELO3C022499 | 307.3 | 79.1 | 0.3 | 0.0000 | 0.0000 | 307.3 | 4.5 | 0.2 | 0.0003 | 0.0391 | 16.3 | 136.2 | 8.4 | 0.0000 | 0.0000 | XP_002320721 | predicted protein [*Populus trichocarpa*] |
| 1 | BBB | MELO3C010773 | 65.0 | 17.9 | 0.3 | 0.0002 | 0.0116 | 65.0 | 40.3 | 0.4 | 0.0001 | 0.0217 | 9.7 | 90.7 | 9.4 | 0.0000 | 0.0000 | ABH02912 | MYB transcription factor MYB71 [*Glycine max*] |
| 1 | BBB | MELO3C002508 | 866.4 | 366.8 | 0.4 | 0.0003 | 0.0166 | 866.4 | 295.6 | 0.5 | 0.0001 | 0.0164 | 302.3 | 988.6 | 3.3 | 0.0000 | 0.0011 | AAD33596 | thioredoxin h [*Hevea brasiliensis*] |
| 1 | BBB | MELO3C022116 | 1,000.9 | 32.6 | 0.0 | 0.0000 | 0.0000 | 21.3 | 4.3 | 0.2 | 0.0020 | 0.1745 | 6.7 | 1,514.5 | 225.7 | 0.0000 | 0.0000 | XP_002519929 | heat-shock protein, putative [*Ricinus communis*] |
| 2 | BB | MELO3C018485 | 681.3 | 37.2 | 0.1 | 0.0000 | 0.0000 | 681.3 | 13.7 | 0.5 | 0.0565 | 1.0000 | 11.9 | 437.1 | 36.8 | 0.0000 | 0.0000 | XP_002521274 | heat-shock protein, putative [*Ricinus communis*] |
| 2 | BB | MELO3C025135 | 1,245.0 | 103.4 | 0.1 | 0.0000 | 0.0000 | 1,245.0 | 7.6 | 0.5 | 0.1667 | 1.0000 | 11.3 | 467.9 | 41.4 | 0.0000 | 0.0000 | AAD49336 | low molecular weight heat-shock protein [*Nicotiana tabacum*] |
| 2 | BB | MELO3C018023 | 1,232.5 | 184.1 | 0.1 | 0.0000 | 0.0000 | 1,232.5 | 59.2 | 0.5 | 0.0041 | 0.2815 | 108.7 | 295.7 | 2.7 | 0.0005 | 0.0291 | ADN33815 | sterol regulatory element-binding protein site 2 protease [*Cucumis melo*] |
| 2 | BB | MELO3C004433 | 1,794.3 | 279.2 | 0.2 | 0.0000 | 0.0000 | 1,794.3 | 352.3 | 0.6 | 0.0024 | 0.2014 | 532.9 | 1,263.8 | 2.4 | 0.0012 | 0.0608 | XP_002531446 | calcium ion binding |

TABLE 2-continued

| C | Sub-C | ID | CEZ sf | CEZ WT | WT/sf | P | Adj P | ED sf | ED WT | WT/sf | P | Adj P | NY sf | NY WT | WT/sf | P | Adj P | ACC | DESC |
|---|---|---|---|---|---|---|---|---|---|---|---|---|---|---|---|---|---|---|---|
| 2 | BB | MELO3C024086 | 1,469.6 | 255.5 | 0.2 | 0.0000 | 0.0000 | 1,469.6 | 73.1 | 0.6 | 0.0418 | 1.0000 | 122.4 | 446.5 | 3.6 | 0.0000 | 0.0006 | XP_002526446 | protein, putative [*Ricinus communis*] |
| 2 | BB | MELO3C006536 | 415.6 | 62.4 | 0.2 | 0.0000 | 0.0000 | 415.6 | 24.7 | 0.4 | 0.0037 | 0.2635 | 30.0 | 185.6 | 6.2 | 0.0000 | 0.0000 | NP_001148098 | heat shock protein, putative [*Ricinus communis*] heat shock 70 kDa protein 1 [*Zea mays*] |
| 2 | BB | MELO3C015515 | 60.2 | 393.2 | 6.5 | 0.0000 | 0.0000 | 60.2 | 1,846.2 | 1.7 | 0.0066 | 0.3958 | 456.6 | 1,031.6 | 2.3 | 0.0016 | 0.0774 | Q9ZRA4 | RecName: Full = Auxin-binding protein ABP19a; Flags: Precursor |
| 2 | BB | MELO3C003177 | 271.8 | 40.9 | 0.2 | 0.0000 | 0.0000 | 271.8 | 43.0 | 0.4 | 0.0026 | 0.2108 | 40.0 | 73.1 | 1.8 | 0.0759 | 1.0000 | XP_002534074 | Peptide transporter, putative [*Ricinus communis*] |
| 2 | BB | MELO3C016897 | 5,196.4 | 1,190.0 | 0.2 | 0.0000 | 0.0000 | 5,196.4 | 70.3 | 0.6 | 0.0156 | 0.6527 | 111.7 | 6,477.3 | 58.0 | 0.0000 | 0.0000 | ACV93250 | CII small heat shock protein 1 [*Prunus salicina*] |
| 2 | BB | MELO3C015804 | 1,495.2 | 372.0 | 0.2 | 0.0000 | 0.0000 | 1,495.2 | 19.5 | 0.6 | 0.0751 | 1.0000 | 29.8 | 500.7 | 16.8 | 0.0000 | 0.0000 | XP_002517070 | Heat shock factor protein HSF30, putative [*Ricinus communis*] |
| 2 | BB | MELO3C003331 | 283.8 | 62.0 | 0.2 | 0.0000 | 0.0000 | 283.8 | 31.0 | 0.6 | 0.1165 | 1.0000 | 24.3 | 29.0 | 1.2 | 0.6588 | 1.0000 | XP_002873020 | hypothetical protein ARALYDRAFT_486956 [*Arabidopsis lyrata* subsp. *lyrata*] |
| 2 | BB | MELO3C003331 | 283.8 | 62.0 | 0.2 | 0.0000 | 0.0000 | 283.8 | 31.0 | 0.6 | 0.1165 | 1.0000 | 24.3 | 29.0 | 1.2 | 0.6588 | 1.0000 | XP_002873020 | hypothetical protein ARALYDRAFT_486956 [*Arabidopsis lyrata*] |

TABLE 2-continued

| C | Sub-C | ID | CEZ sf | CEZ WT | WT/sf | P | Adj P | ED sf | ED WT | WT/sf | P | Adj P | NY sf | NY WT | WT/sf | P | Adj P | ACC | DESC |
|---|---|---|---|---|---|---|---|---|---|---|---|---|---|---|---|---|---|---|---|
| 2 | BB | MELO3C004434 | 685.6 | 185.5 | 0.3 | 0.0000 | 0.0000 | 685.6 | 227.2 | 0.4 | 0.0001 | 0.0155 | 308.5 | 697.6 | 2.3 | 0.0024 | 0.1076 | ADN34124 | lyrata subsp. lyrata] serine-rich protein [Cucumis melo subsp. melo] |
| 2 | BB | MELO3C019254 | 90.8 | 284.0 | 3.1 | 0.0000 | 0.0009 | 90.8 | 48.8 | 1.6 | 0.1036 | 1.0000 | 82.6 | 49.9 | 0.6 | 0.1211 | 1.0000 | BAC79616 | putative Septum-promoting GTP-binding protein 1 (GTPase spg1) [Oryza sativa] |
| 2 | BB | MELO3C023497 | 25.5 | 2.0 | 0.1 | 0.0000 | 0.0012 | 25.5 | 11.1 | 0.6 | 0.2883 | 1.0000 | 13.0 | 22.9 | 1.8 | 0.2333 | 1.0000 | XP_002531706 | Nonspecific lipid-transfer protein precursor, putative [Ricinus communis] |
| 2 | BB | MELO3C005923 | 303.6 | 106.8 | 0.4 | 0.0000 | 0.0027 | 303.6 | 61.0 | 0.3 | 0.0000 | 0.0001 | 96.1 | 166.3 | 1.7 | 0.0643 | 0.9395 | XP_002867485 | chloroplast small heat shock protein [Arabidopsis lyrata subsp. lyrata] |
| 2 | BB | MELO3C025085 | 528.1 | 198.5 | 0.4 | 0.0001 | 0.0039 | 528.1 | 26.7 | 0.5 | 0.0131 | 0.5872 | 39.0 | 263.1 | 6.7 | 0.0000 | 0.0000 | BAG09378 | peroxisomal small heat shock protein [Glycine max] |
| 2 | BB | MELO3C005629 | 175.4 | 58.9 | 0.3 | 0.0001 | 0.0060 | 175.4 | 149.4 | 2.2 | 0.0010 | 0.1065 | 55.5 | 158.3 | 2.9 | 0.0004 | 0.0271 | ABH08746 | CBF/DREB-like transcription factor 1 [Citrus trifoliata] |
| 2 | BB | MELO3C002513 | 519.6 | 206.1 | 0.4 | 0.0001 | 0.0093 | 519.6 | 50.8 | 0.5 | 0.0077 | 0.4330 | 82.5 | 288.2 | 3.5 | 0.0000 | 0.0016 | NP_567623 | Aldolase-type TIM barrel family protein |

TABLE 2-continued

| C | Sub-C | ID | CEZ sf | CEZ WT | WT/sf | P | Adj P | ED sf | ED WT | WT/sf | P | Adj P | NY sf | NY WT | WT/sf | P | Adj P | ACC | DESC |
|---|---|---|---|---|---|---|---|---|---|---|---|---|---|---|---|---|---|---|---|
| 2 | BB | MELO3C024263 | 182.0 | 67.9 | 0.4 | 0.0003 | 0.0167 | 182.0 | 54.9 | 0.2 | 0.0000 | 0.0000 | 79.7 | 154.0 | 1.9 | 0.0250 | 0.5632 | XP_002515999 | tonoplast intrinsic protein, putative [*Ricinus communis*] |
| 2 | B | MELO3C020963 | 338.8 | 87.0 | 0.3 | 0.0000 | 0.0000 | 338.8 | 155.9 | 1.7 | 0.0150 | 0.6359 | 510.2 | 106.9 | 0.2 | 0.0000 | 0.0000 | XP_002533354 | WRKY transcription factor, putative [*Ricinus communis*] |
| 2 | B | MELO3C021168 | 108.2 | 246.0 | 2.3 | 0.0011 | 0.0495 | 108.2 | 114.0 | 2.3 | 0.0009 | 0.0974 | 125.8 | 75.2 | 0.6 | 0.0921 | 1.0000 | XP_002511954 | Esterase precursor, putative [*Ricinus communis*] |
| 2 | B | MELO3C011948 | 68.4 | 20.8 | 0.3 | 0.0004 | 0.0201 | 68.4 | 21.4 | 1.7 | 0.2273 | 1.0000 | 33.6 | 13.0 | 0.4 | 0.0258 | 0.5767 | XP_002530026 | leucine-rich repeat-containing protein, putative [*Ricinus communis*] |
| 2 | B | MELO3C003911 | 261.9 | 112.4 | 0.4 | 0.0009 | 0.0401 | 261.9 | 294.5 | 1.8 | 0.0042 | 0.2851 | 463.2 | 268.1 | 0.6 | 0.0441 | 0.7727 | XP_002512304 | copine, putative [*Ricinus communis*] |

[*Arabidopsis thaliana*]

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Anders S (2010). Analysing RNA-Seq data with the DESeq package. Molecular biology, 1-17.

Cabezas J A, Cervera M T, Ruiz-García L, Carreño J, Martínez-Zapater J M (2006) A genetic analysis of seed and berry weight in grapevine. Genome, 49: 1572-1585.

Cowan A K, Cripps R F, Richings E W, Taylor N J (2001) Fruit size: towards an understanding of the metabolic control of fruit growth using avocado as a model system. Physiologia Plantarum, 111: 127-136.

Dathan N, Zaccaro L, Esposito S, Isernia C, Omichinski J G, Riccio A, . . . Pedone, P. V (2002). The *Arabidopsis* SUPERMAN protein is able to specifically bind DNA through its single Cys2-His2 zinc finger motif. Nucleic acids research, 30: 4945-4951

DePristo M A, Banks E, Poplin R, Garimella K V, Maguire J R, Hartl C, . . . & Daly M J (2011) A framework for variation discovery and genotyping using next-generation DNA sequencing data. Nature genetics, 43(5), 491-498.

Gidoni D, Carmi N (2007) Mutagenesis for seedlessness in Citrus. Israel J. Plant Sci. 55: 133-135.

Grumet R, Katzir N, Little H A, Portnoy V, Burger Y (2007) New insights into reproductive development in melon (*Cucumis melo* L.). Intl J Plant Developmental Biol: 253-264.

Jiang C J, Aono M, Tamaoki M, Maeda S, Sugano S, Mori M, Takatsuji H (2008) SAZ, a new SUPERMAN-like protein, negatively regulates a subset of ABA-responsive genes in *Arabidopsis*. Molecular Genetics and Genomics, 279: 183-192.

Kim D, Pertea G, Trapnell C, Pimentel H, Kelley R, Salzberg S L (2013) TopHat2: accurate alignment of transcriptomes in the presence of insertions, deletions and gene fusions. Genome Biol, 14: R36.

Klug A (2010) The discovery of zinc fingers and their applications in gene regulation and genome manipulation. Annual review of biochemistry, 79: 213-231.

Klug A, Schwabe J W (1995) Protein motifs 5. Zinc fingers. The FASEB journal, 9: 597-604.

Lee M S, Gippert G P, Soman K V, Case D A, Wright P E (1989) Three-dimensional solution structure of a single zinc finger DNA-binding domain. Science, 245: 635-637.

Liu Q L, Xu K D, Ma N, Zhao L J, Xi L (2014) Overexpression of a novel *chrysanthemum* SUPERMAN-like gene in tobacco affects lateral bud outgrowth and flower organ development. Plant Physiology and Biochemistry 77: 1-6.

Mejía N, Soto B, Guerrero M, Casanueva X, Houel C, de los Ángeles Miccono, M, Adam-Blondon A F (2011) Molecular, genetic and transcriptional evidence for a role of VvAGL11 in stenospermocarpic seedlessness in grapevine. BMC plant biology, 11: 57.

Menda N, Semel Y, Peled D, Eshed Y, Zamir D (2004) In silico screening of a saturated mutation library of tomato. Plant J. 38:861-872.

Papadopoulou E, Little H A, Hammar S A, Grumet R (2005) Effect of modified endogenous ethylene production on sex expression, bisexual flower development and fruit production in melon (*Cucumis melo* L.). Sexual plant reproduction, 18: 131-142.

Tadmor Y, Larkov O, Meir A, Minkoff M, Lastochkin E, Edelstein E, Levin S, Wong J, Rocheford T, and Lewinsohn E. (2000) Reversed-phase high performance liquid chromatographic determination of vitamin E components in maize kernels. Phytochem. Anal. 11: 370-374

Tadmor Y, King S, Levi A, Davis A, Meir A, Wasserman B, Hirschberg J, and Lewinsohn E. (2005) Comparative fruit colouration in watermelon and tomato. Food Res. Int. 38: 837-841.

Tadmor Y, Katzir N, Meir A, Yaniv-Yaakov A, Sa'ar U, Baumkoler F, Lavee T, Lewinsohn E, Schaffer A A, Burger J (2007) Induced mutagenesis to augment the natural genetic variability of melon (*Cucumis melo* L.). Israel J. Plant Sci. 55: 159-169.

What is claimed is:

1. A *Cucumis melo* plant or a part thereof carrying a loss of function mutation in the MELO3 C009603 gene, wherein the plant bears more than 12 fruit, said fruit being seedless.

2. A *Cumumis melo* plant carrying a loss of function mutation in the MELO3C009603 gene in a heterozygous form such that upon self-pollination, 25% of F1 bear more than 12 fruit, said fruit being seedless.

3. The plant of claim 1, bearing more than 15 fruit.

4. The plant of claim 1, bearing more than 20 fruit.

5. The plant of claim 1, wherein the weight of total fruit of said plant is greater than the weight of total fruit of a wild-type *Cucumis melo* plant.

6. The plant of claim 1, being of a variety *C. melo Cantalupensis*.

7. The plant of claim 1, wherein both alleles of MELO3 C009603 of the genome of the plant have a loss of function mutation that results in a seedless trait.

8. The plant of claim 7, wherein both alleles of said MELO3 C009603 have an F/I mutation at position 97 thereof.

9. The plant of claim 7, wherein the polynucleotide sequence of said MELO3 C009603 is as set forth in SEQ ID NO: 7.

10. The plant of claim 1, wherein the polypeptide sequence of MELO3 C009603 is as set forth in SEQ ID NO: 8.

11. A cutting of a *C. melo* plant of the plant of claim 1.

12. The plant part of claim 1, being selected from the group consisting of roots, stems, leaves, cotyledons, flowers, fruit, embryos and pollen.

13. A seed of the plant of claim 2.

14. A cell having the genome of the plant of claim 1.

15. A culture comprising a plurality the cells of claim 14.

16. The plant part of claim 1, selected from the group consisting of roots, stems, leaves, cotyledons, flowers, fruit, embryos and pollen.

17. A method of breeding a first *C. melo* comprising crossing the plant of claim 1 with a second *C. melo* plant, thereby breeding the *C. melo*.

18. The method of claim 17, wherein said crossing comprises pollinating.

19. The method of claim 17, wherein a subspecies of said *melo* plant is selected from the group consisting of *melo Cantalupensis*, Noy Yizre'el, Ein Dor and Piel De Sapo.

20. A plurality of *C. melo* seeds of the plant of claim 2.

21. A hybrid seed produced by the method of claim 17, wherein the seed comprises a loss of function mutation in the MELO3009603 gene.

22. A hybrid plant, or parts thereof, produced by growing the hybrid seed of claim 20.

23. A method of growing the plant of claim 1 comprising vegetatively propagating the plant, thereby growing the plant.

* * * * *

UNITED STATES PATENT AND TRADEMARK OFFICE
CERTIFICATE OF CORRECTION

PATENT NO. : 10,111,395 B2
APPLICATION NO. : 15/125172
DATED : October 30, 2018
INVENTOR(S) : Yaakov Tadmor et al.

It is certified that error appears in the above-identified patent and that said Letters Patent is hereby corrected as shown below:

On the Title Page

Item (73) Assignee, at Line 3:
"Organizatin" should be changed to -- Organization --

Signed and Sealed this
Twenty-sixth Day of February, 2019

Andrei Iancu
*Director of the United States Patent and Trademark Office*